United States Patent
Jacq et al.

(10) Patent No.: US 10,690,656 B2
(45) Date of Patent: Jun. 23, 2020

(54) METHODS OF SCREENING AND TREATMENT WITH USP4 INHIBITORS

(71) Applicants: MISSION THERAPEUTICS LIMITED, Cambridge (GB); CAMBRIDGE ENTERPRISE LIMITED, Cambridge (GB)

(72) Inventors: Xavier Jacq, Cambridge (GB); Helen Robinson, Cambridge (GB); Yaara Ofir-Rosenfeld, Cambridge (GB); Stephen Jackson, Cambridge (GB); Paul Wijnhoven, Cambridge (GB); Ryotaro Nishi, Cambridge (GB)

(73) Assignees: MISSION THERAPEUTICS LIMITED, Cambridge (GB); CAMBRIDGE ENTERPRISE LIMITED, Cambridge (GB)

(*) Notice: Subject to any disclaimer, the term of this patent is extended or adjusted under 35 U.S.C. 154(b) by 141 days.

(21) Appl. No.: 15/549,227

(22) PCT Filed: Feb. 29, 2016

(86) PCT No.: PCT/GB2016/050517
§ 371 (c)(1),
(2) Date: Aug. 7, 2017

(87) PCT Pub. No.: WO2016/135513
PCT Pub. Date: Sep. 1, 2016

(65) Prior Publication Data
US 2019/0033292 A1    Jan. 31, 2019

(30) Foreign Application Priority Data
Feb. 27, 2015 (GB) .................................. 1503371.5

(51) Int. Cl.
*C12N 15/11* (2006.01)
*C07H 21/02* (2006.01)
(Continued)

(52) U.S. Cl.
CPC ..... *G01N 33/5008* (2013.01); *A61K 31/4745* (2013.01); *A61K 31/502* (2013.01);
(Continued)

(58) Field of Classification Search
CPC ........... G01N 2500/02; G01N 2800/52; C12N 15/113; C12N 15/1138; A61K 31/00; C12Q 2600/158
See application file for complete search history.

(56) References Cited

U.S. PATENT DOCUMENTS

2008/0038768 A1    2/2008  Filipuzzi et al.
2009/0023149 A1    1/2009  Knudsen

FOREIGN PATENT DOCUMENTS

JP    2012036150 A    2/2012
WO    2009037527 A2    3/2009
WO    2016011906 A1    1/2016

OTHER PUBLICATIONS

Cancer Research Wales, https://www.cancerresearchwales.co.uk/blog/no-two-cancers-are-the-same, downloaded on Sep. 25, 2019.*
(Continued)

*Primary Examiner* — Terra C Gibbs

(57) ABSTRACT

The present application relates to materials and methods for exploiting synthetic lethality and/or chemo-sensitisation in DNA damage response (DDR) pathways. In particular, the application relates to ubiquitin hydrolase protein Ubiquitin Specific Protease 4 (USP4) and its association with DDR pathways. Further, the use of USP4 inhibitors in the treatment of cancer and methods of screening is described, in particular, use of inhibitors of USP4 in the treatment of (Continued)

tumours defective in double-strand break repair (DSBR) and/or tumours resistant to platinum-based chemotherapy, or to sensitise, i.e. chemosensitise or radiosensitise tumours to other therapeutic agents.

9 Claims, 11 Drawing Sheets

Specification includes a Sequence Listing.

(51) Int. Cl.
  *C07H 21/04*   (2006.01)
  *A61K 48/00*   (2006.01)
  *G01N 33/50*   (2006.01)
  *A61K 31/4745*   (2006.01)
  *A61K 31/502*   (2006.01)
  *A61K 31/7048*   (2006.01)
  *A61K 41/00*   (2020.01)
  *C12Q 1/6886*   (2018.01)
  *C12N 9/64*   (2006.01)
  *A61K 39/00*   (2006.01)

(52) U.S. Cl.
  CPC ...... *A61K 31/7048* (2013.01); *A61K 41/0038* (2013.01); *C12N 9/6472* (2013.01); *C12Q 1/6886* (2013.01); *A61K 2039/505* (2013.01); *C12Q 2600/106* (2013.01); *G01N 2333/948* (2013.01); *G01N 2500/02* (2013.01)

(56) References Cited

OTHER PUBLICATIONS

Stephens et al. (Nature, 2012 vol. 486:400-406).*
The International Search Report and Written Opinion, dated Jul. 12, 2016, in the corresponding PCT Appl. No. PCT/GB2016/050517.
Zhang et al: "USP4 is regulated by AKT phosphorylation and directly deubiquitylates TGF-[beta] type I receptor", Nature Cell Biology, vol. 14, No. 7, Jun. 17, 2012(Jun. 17, 2012), pp. 717-726.
Zhang et al: "USP4 inhibits p53 through deubiquitinating and stabilizing ARF-BP1", EMBO Journal., vol. 30, No. 11, Jun. 1, 2011(Jun. 1, 2011), pp. 2177-2189.
Xiao et al: "Ubiquitin-specific protease 4 (USP4) targets TRAF2 and TRAF6 for deubiquitination and inhibits TNF [alpha]-induced cancer cell migration", Biochem J. Feb. 1, 2012;441(3):979-86.
Velazquez-Fernandez et al., "Expression profiling of adrenocortical neoplasms suggests a molecular signature of malignancy," Surgery. Dec. 2005;138(6):1087-94.
Hou et al., "Ubiquitin-specific protease 4 promotes TNF-a-induced apoptosis by deubiquitination of RIP1 in head and neck squamous cell carcinoma," FEBS Letters 587 (2013) 311-316.
Jacq et al., "Deubiquitylating Enzymes and DNA Damage Response Pathways," Cell Biochem Biophys (2013) 67:25-43.
Liu et al., "The Deubiquitylating Enzyme USP4 Cooperates with CtIP in DNA Double-Strand Break End Resection," Cell Reports 13,93-107, Oct. 6, 2015.
Nijman et al., "Potential of the Synthetic Lethality Principle," Science. Nov. 15, 2013;342(6160):809-11.
Norikura et al., "Anticancer Activities of Thelephantin 0 and Vialinin A Isolated from Thelephora aurantiotincta," J Agric Food Chem. Jul. 13, 2011;59(13):6974-9.
Wijnhoven et al, "USP4 Auto-Deubiquitylation Promotes Homologous Recombination," Molecular Cell 60, 362-373, Nov. 5, 2015.
Wada et al., "Oncogenic protein UnpEL/Usp4 deubiquitinates Ro52 by its isopeptidase activity," Biochemical and Biophysical Research Communications 339 (2006) 731-736.
Wiltshire et al, "Sensitivity to poly(ADP-ribose) polymerase (PARP) inhibition identifies ubiquitin-specific peptidase 11 (USP11) as a regulator of DNA double-strand break repair," J Biol Chem. May 7, 2010;285(19):14565-71.
Okada et al., "Vialinin A is a ubiquitin-specific peptidase inhibitor," Bioorg. Med. Chem. Lett. 23 (2013) 4328-4331.
Shaheen et al., "Synthetic lethality: exploiting the addiction of cancer to DNA repair," Blood. Jun. 9, 2011;117(23):6074-82.

* cited by examiner

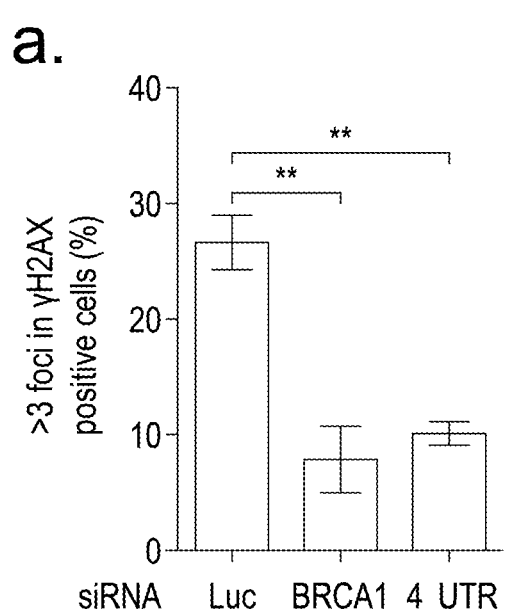
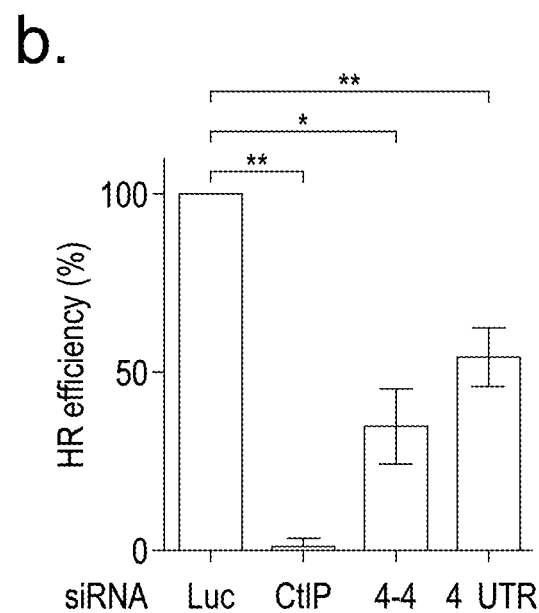
Fig. 12
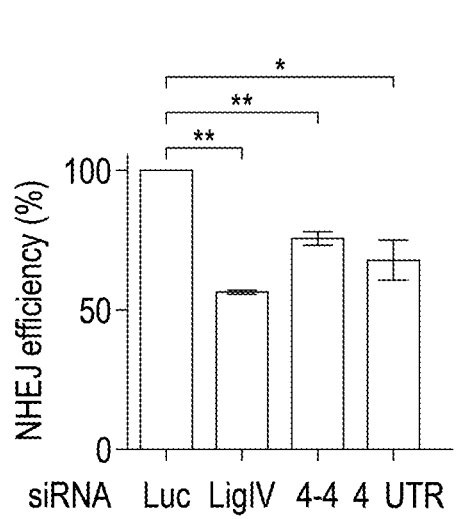
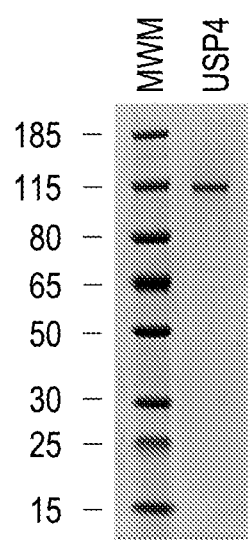
Fig. 13
Fig. 14

SEQUENCE LISTING

<160> NUMBER OF SEQ ID NOS: 12

<210> SEQ ID NO 1
<211> LENGTH: 963
<212> TYPE: PRT
<213> ORGANISM: Homo sapiens
<220> FEATURE:
<223> OTHER INFORMATION: USP4 protein

<400> SEQUENCE: 1

```
Met Ala Glu Gly Gly Gly Cys Arg Glu Arg Pro Asp Ala Glu Thr Gln
1               5                   10                  15

Lys Ser Glu Leu Gly Pro Leu Met Arg Thr Thr Leu Gln Arg Gly Ala
            20                  25                  30

Gln Trp Tyr Leu Ile Asp Ser Arg Trp Phe Lys Gln Trp Lys Lys Tyr
        35                  40                  45

Val Gly Phe Asp Ser Trp Asp Met Tyr Asn Val Gly Glu His Asn Leu
    50                  55                  60

Phe Pro Gly Pro Ile Asp Asn Ser Gly Leu Phe Ser Asp Pro Glu Ser
65                  70                  75                  80

Gln Thr Leu Lys Glu His Leu Ile Asp Glu Leu Asp Tyr Val Leu Val
                85                  90                  95

Pro Thr Glu Ala Trp Asn Lys Leu Leu Asn Trp Tyr Gly Cys Val Glu
            100                 105                 110

Gly Gln Gln Pro Ile Val Arg Lys Val Val Glu His Gly Leu Phe Val
        115                 120                 125

Lys His Cys Lys Val Glu Val Tyr Leu Leu Glu Leu Lys Leu Cys Glu
    130                 135                 140

Asn Ser Asp Pro Thr Asn Val Leu Ser Cys His Phe Ser Lys Ala Asp
145                 150                 155                 160

Thr Ile Ala Thr Ile Glu Lys Glu Met Arg Lys Leu Phe Asn Ile Pro
                165                 170                 175

Ala Glu Arg Glu Thr Arg Leu Trp Asn Lys Tyr Met Ser Asn Thr Tyr
            180                 185                 190

Glu Gln Leu Ser Lys Leu Asp Asn Thr Val Gln Asp Ala Gly Leu Tyr
        195                 200                 205

Gln Gly Gln Val Leu Val Ile Glu Pro Gln Asn Glu Asp Gly Thr Trp
    210                 215                 220

Pro Arg Gln Thr Leu Gln Ser Lys Ser Ser Thr Ala Pro Ser Arg Asn
225                 230                 235                 240

Phe Thr Thr Ser Pro Lys Ser Ala Ser Pro Tyr Ser Ser Val Ser
                245                 250                 255

Ala Ser Leu Ile Ala Asn Gly Asp Ser Thr Ser Thr Cys Gly Met His
            260                 265                 270

Ser Ser Gly Val Ser Arg Gly Gly Ser Gly Phe Ser Ala Ser Tyr Asn
        275                 280                 285

Cys Gln Glu Pro Pro Ser Ser His Ile Gln Pro Gly Leu Cys Gly Leu
    290                 295                 300

Gly Asn Leu Gly Asn Thr Cys Phe Met Asn Ser Ala Leu Gln Cys Leu
305                 310                 315                 320

Ser Asn Thr Ala Pro Leu Thr Asp Tyr Phe Leu Lys Asp Glu Tyr Glu
                325                 330                 335

Ala Glu Ile Asn Arg Asp Asn Pro Leu Gly Met Lys Gly Glu Ile Ala
            340                 345                 350

Glu Ala Tyr Ala Glu Leu Ile Lys Gln Met Trp Ser Gly Arg Asp Ala
```

```
            355                 360                 365
His Val Ala Pro Arg Met Phe Lys Thr Gln Val Gly Arg Phe Ala Pro
370                 375                 380

Gln Phe Ser Gly Tyr Gln Gln Gln Asp Ser Gln Glu Leu Leu Ala Phe
385                 390                 395                 400

Leu Leu Asp Gly Leu His Glu Asp Leu Asn Arg Val Lys Lys Lys Pro
                405                 410                 415

Tyr Leu Glu Leu Lys Asp Ala Asn Gly Arg Pro Asp Ala Val Val Ala
                420                 425                 430

Lys Glu Ala Trp Glu Asn His Arg Leu Arg Asn Asp Ser Val Ile Val
                435                 440                 445

Asp Thr Phe His Gly Leu Phe Lys Ser Thr Leu Val Cys Pro Glu Cys
                450                 455                 460

Ala Lys Val Ser Val Thr Phe Asp Pro Phe Cys Tyr Leu Thr Leu Pro
465                 470                 475                 480

Leu Pro Leu Lys Lys Asp Arg Val Met Glu Val Phe Leu Val Pro Ala
                485                 490                 495

Asp Pro His Cys Arg Pro Thr Gln Tyr Arg Val Thr Val Pro Leu Met
                500                 505                 510

Gly Ala Val Ser Asp Leu Cys Glu Ala Leu Ser Arg Leu Ser Gly Ile
                515                 520                 525

Ala Ala Glu Asn Met Val Val Ala Asp Val Tyr Asn His Arg Phe His
530                 535                 540

Lys Ile Phe Gln Met Asp Glu Gly Leu Asn His Ile Met Pro Arg Asp
545                 550                 555                 560

Asp Ile Phe Val Tyr Glu Val Cys Ser Thr Ser Val Asp Gly Ser Glu
                565                 570                 575

Cys Val Thr Leu Pro Val Tyr Phe Arg Glu Arg Lys Ser Arg Pro Ser
                580                 585                 590

Ser Thr Ser Ser Ala Ser Ala Leu Tyr Gly Gln Pro Leu Leu Leu Ser
                595                 600                 605

Val Pro Lys His Lys Leu Thr Leu Glu Ser Leu Tyr Gln Ala Val Cys
                610                 615                 620

Asp Arg Ile Ser Arg Tyr Val Lys Gln Pro Leu Pro Asp Glu Phe Gly
625                 630                 635                 640

Ser Ser Pro Leu Glu Pro Gly Ala Cys Asn Gly Ser Arg Asn Ser Cys
                645                 650                 655

Glu Gly Glu Asp Glu Glu Glu Met Glu His Gln Glu Glu Gly Lys Glu
                660                 665                 670

Gln Leu Ser Glu Thr Glu Gly Ser Gly Glu Asp Glu Pro Gly Asn Asp
                675                 680                 685

Pro Ser Glu Thr Thr Gln Lys Lys Ile Lys Gly Gln Pro Cys Pro Lys
                690                 695                 700

Arg Leu Phe Thr Phe Ser Leu Val Asn Ser Tyr Gly Thr Ala Asp Ile
705                 710                 715                 720

Asn Ser Leu Ala Ala Asp Gly Lys Leu Leu Lys Leu Asn Ser Arg Ser
                725                 730                 735

Thr Leu Ala Met Asp Trp Asp Ser Glu Thr Arg Arg Leu Tyr Tyr Asp
                740                 745                 750

Glu Gln Glu Ser Glu Ala Tyr Glu Lys His Val Ser Met Leu Gln Pro
                755                 760                 765

Gln Lys Lys Lys Lys Thr Thr Val Ala Leu Arg Asp Cys Ile Glu Leu
                770                 775                 780
```

```
Phe Thr Thr Met Glu Thr Leu Gly Glu His Asp Pro Trp Tyr Cys Pro
785                 790                 795                 800

Asn Cys Lys Lys His Gln Gln Ala Thr Lys Lys Phe Asp Leu Trp Ser
            805                 810                 815

Leu Pro Lys Ile Leu Val Val His Leu Lys Arg Phe Ser Tyr Asn Arg
        820                 825                 830

Tyr Trp Arg Asp Lys Leu Asp Thr Val Val Glu Phe Pro Ile Arg Gly
            835                 840                 845

Leu Asn Met Ser Glu Phe Val Cys Asn Leu Ser Ala Arg Pro Tyr Val
850                 855                 860

Tyr Asp Leu Ile Ala Val Ser Asn His Tyr Gly Ala Met Gly Val Gly
865                 870                 875                 880

His Tyr Thr Ala Tyr Ala Lys Asn Lys Leu Asn Gly Lys Trp Tyr Tyr
            885                 890                 895

Phe Asp Asp Ser Asn Val Ser Leu Ala Ser Glu Asp Gln Ile Val Thr
            900                 905                 910

Lys Ala Ala Tyr Val Leu Phe Tyr Gln Arg Arg Asp Asp Glu Phe Tyr
            915                 920                 925

Lys Thr Pro Ser Leu Ser Ser Ser Gly Ser Ser Asp Gly Gly Thr Arg
            930                 935                 940

Pro Ser Ser Ser Gln Gln Gly Phe Gly Asp Asp Glu Ala Cys Ser Met
945                 950                 955                 960

Asp Thr Asn

<210> SEQ ID NO 2
<211> LENGTH: 4120
<212> TYPE: RNA
<213> ORGANISM: Homo sapiens
<220> FEATURE:
<221> NAME/KEY: source
<222> LOCATION: 1..4120
<223> OTHER INFORMATION: /organism="Homo sapiens"
      /note="USP4 mRNA "
      /mol_type="unassigned RNA"

<400> SEQUENCE: 2
gtgcgtgcgt gggcgcggtc tatagcacgc cgcgcgcggg gcggatgtcc gggccggctg      60
ggccggggcc gcggaggaga tggcggaagg tggaggctgc cgtgagcgac cggatgcgga     120
gactcagaag tccgagcttg gacccttaat gaggaccaca ctccaacgcg gggcgcagtg     180
gtatcttatt gacagccggt ggttcaagca gtggaagaag tatgtgggct ttgacagctg     240
ggacatgtac aatgtgggtg aacataacct atttcctggc ccaatagaca actctgggct     300
attttcagat cctgagagtc agaccttgaa agaacactta attgatgaat tggactatgt     360
attggtccct accgaggcgt ggaataaact actaaactgg tacggctgtg tagaaggcca     420
gcaacccatc gtcagaaaag ttgtggagca tggcctgttt gtcaagcact gcaaagtcga     480
ggtgtatttg ctggaactga agctctgtga aacagtgac cccaccaatg tgctgagttg     540
ccatttcagc aaggcagaca ccattgcaac catcgagaaa gagatgcgga agctattcaa     600
catccctgcg gagcgtgaaa cacggctctg aacaaatac atgagcaaca cctacgagca     660
gttgagcaag ctagacaaca ctgtccagga tgctgggcta taccagggtc aggtgctagt     720
aattgagcct caaatgaag atggcacatg gcccaggcag accttgcagt caaaatcaag     780
cactgcgcct agcagaaatt ttactacctc tccaaaatca tcagcaagtc cctattcctc     840
agtgtctgcc tctctcattg caaatggtga tagcactagc acctgtggga tgcacagttc     900
```

```
cggtgtcagc aggggtggat ctggctttc tgcttcgtat aattgtcagg agccaccatc    960
ctctcatata caacctgggc tctgtggact tggaaacctg ggaaacacct gcttcatgaa   1020
ctccgctttg cagtgtttga gcaacactgc accactgact gactactttc tcaaagatga   1080
gtatgaagcc gaaatcaaca gagacaaccc tctggggatg aaaggggaaa ttgcagaagc   1140
ctatgctgaa ctcattaagc agatgtggtc tggaagggac gcccatgtgg cacctcgcat   1200
gttcaaaact caagtaggac gttttgctcc tcaattttct ggctaccagc aacaagattc   1260
tcaggagctg ctggcctttc ttctagatgg attgcatgaa gatctgaacc gggtaaagaa   1320
aaagccctac ttggagctga aggatgccaa tgggcggcca gatgcggtgg tggcaaagga   1380
agcctgggag aatcacaggt tgaggaatga ttctgtgatt gtggatactt ccatggcct    1440 cttcaaatct actttggttt gcccagaatg tgctaaggtt tctgtgacct ttgacccatt   1500
ttgctatcta acgctgccac tgcccttgaa gaaagatcga gttatggagg ttttcctggt   1560
tcctgctgac cctcactgca gacctactca gtaccgtgtg actgtgccgc tgatgggggc   1620
tgtgtccgac ctgtgcgagg ctctctccag gctgtctggc attgctgcag aaaatatggt   1680
ggtcgcagat gtgtataatc accgattcca caaaattttc caaatggatg aaggtttaaa   1740
ccacatcatg cctcgggatg acattttcgt gtacgaggtc tgcagcactt ccgtggatgg   1800
ctcggaatgt gtcacgcttc cagtctactt caggagagg aagtccaggc catcaagcac   1860
ttcctccgca tcagcgctat atgggcagcc actattgctt tctgtcccca agcacaagtt   1920
aacccttgag tctttgtacc aggctgtttg tgatcgtatc agccgctatg tgaaacagcc   1980
tttacctgat gagtttggca gctcaccctt ggagccaggg gcctgcaatg ctccaggaa   2040 cagctgtgaa ggagaagatg aggaagaaat ggagcatcag gaagaaggca agagcagct   2100 ttcagaaaca gaaggcagtg gggaagatga gccaggaaat gaccccagtg agaccaccca   2160
aaagaagatc aaaggccagc cctgcccaaa aaggcttttt accttcagtc ttgtgaactc   2220
ctatggaaca gctgacataa attcacttgc agctgatgga aaactactta aactcaactc   2280
tcgatctaca ctggccatgg attgggacag tgaaactcgg agactttact atgatgagca   2340
agaatctgag gcctacgaga agcatgtgag catgttgcag cctcagaaga agaagaagac   2400
cacagtggcc ctgagagact gcatcgagct cttcaccacc atggagaccc ttggggagca   2460
tgacccctgg tactgtccca actgtaagaa gcatcaacag ccacaaaaa agtttgacct   2520 atggtccttg cccaagatcc tggtggtcca cctcaaacgt ttctcctaca acagatactg   2580
gagggataag ctcgacacag tcgtagaatt cccaatcaga gggctgaaca tgtccgagtt   2640
tgtctgtaac ctgtcagcaa ggccttatgt gtacgacctc attgccgtgt ccaatcatta   2700
tggagccatg ggggttggcc actacactgc atatgcgaag aacaaactga atggtaaatg   2760
gtattacttt gatgatagca acgtgtccct ggcctctgag gatcagatag tgactaaagc   2820
agcttatgtg ctattttacc aacgtcgaga tgatgaattt tataagacac cttcacttag   2880
cagttctggt tcctctgatg agggacacg accaagcagc tctcagcagg gctttgggga   2940
tgatgaggct tgcagcatgg acaccaacta atgctgactc cacgatcctg ccaccctgta   3000
gcgccagtgt aatcccccag gagaacatct ttgacactct gcagactgct agtgttctgt   3060
ctaaaaacca gacaaggaaa tacccttctt ttatgagcag aaggaaacaa aaaaaaaaa    3120 agaagaccgt ttacctagaa gaagctatgt caagaggctg aattattttt attttttaaac   3180 aggtggtgag aaatttctgt gaaacctgtg aagctgaaaa gggggtggga tgggggtact   3240
```

-continued

```
caatggagta tgtctgatgg atcccgaaga atggagagga acacaggcgc tgagtatgga    3300
gcagcctgga gacccacccc acctgcaggg ctgccctgag cgcctggatt tctggttctg    3360
atgccaatac tagtcacccc aagtagtctg ctcacagtaa cccaaacctc aagtaaactc    3420
ccctttccct cgctatgtgc actgatatgg gtttataatt ttctgaaagt tacccactga    3480
agcccatttc tccgttgagt catcttgtaa tttccagctt tctccccgct aaggaagata    3540
tctagtgttg gggatcctgg cccctcaacc tcctgtggaa cccagcagtt ctgttatatc    3600
ccctgctacc ctagatgaat taagacggtt aaatactgtg tggaactttt attagataac    3660
acacttttta ttagataacg cttaaaggaa gtcagtacat aaaactgccc ggtgctgtgt    3720
cccgtctagt tgtttccatg ttggcttgag aacagaaatc tttgtgggag ttagccggga    3780
aagggctcca gttcatggcg atttagggta gtaatacatt ttggtgttac ccagatgctt    3840
tctagaacgg gttctttcct catccctgcc aagactcttc ccggggcccc cattcgaaag    3900
ccccgtcccc actcccaccg cggggccagc cgctgcgtgt gggcaaggcc ttaaggaacc    3960
ggacgtatgg gtccgggatt ttttgtctga ccttcaacct aatccgtggg ggtttgggc    4020 ctgcgcgggg cacgcgcatg cgatgaccgt tggatgggtc ggcgtcactg cgctgcgggt    4080
gaggacaagg acgtggctgc cgactcgcca aagggggggt                         4120
```

<210> SEQ ID NO 3
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
    /note="Luciferase"
    /mol_type="unassigned RNA"

<400> SEQUENCE: 3
aacguacgcg gaauacuucg a                                              21

<210> SEQ ID NO 4
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
    /note="siUSP4-1"
    /mol_type="unassigned RNA"

<400> SEQUENCE: 4
accgaggcgu ggaauaaacu a                                              21

<210> SEQ ID NO 5
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
    /note="siUSP4-2"
    /mol_type="unassigned RNA"

<400> SEQUENCE: 5
uagaugaauu aagacgguua a                                              21

```
<210> SEQ ID NO 6
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="siUSP4-3"
      /mol_type="unassigned RNA"

<400> SEQUENCE: 6
caggcagacc uugcagucaa a                                              21

<210> SEQ ID NO 7
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="siUSP4-4"
      /mol_type="unassigned RNA"

<400> SEQUENCE: 7
caccuacgag caguugagca a                                              21

<210> SEQ ID NO 8
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="siUSP4 3'-UTR"
      /mol_type="unassigned RNA"

<400> SEQUENCE: 8
uuaaacaggu ggugagaaa                                                 19

<210> SEQ ID NO 9
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="siCtIP"
      /mol_type="unassigned RNA"

<400> SEQUENCE: 9
gcuaaaacag gaacgaauc                                                 19

<210> SEQ ID NO 10
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="siXRCC4"
      /mol_type="unassigned RNA"

<400> SEQUENCE: 10
auauguuggu gaacugaga                                                 19
```

```
<210> SEQ ID NO 11
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="siLigaseIV"
      /mol_type="unassigned RNA"

<400> SEQUENCE: 11
aggaaguauu cucaggaauu a                                              21

<210> SEQ ID NO 12
<211> LENGTH: 18
<212> TYPE: RNA
<213> ORGANISM: Artificial Sequence
<220> FEATURE:
<221> NAME/KEY: source
<222> LOCATION: 1..18
<223> OTHER INFORMATION: /organism="Artificial Sequence"
      /note="siBRCA1"
      /mol_type="unassigned RNA"

<400> SEQUENCE: 12
ggaaccuguc uccacaag                                                  18
```

METHODS OF SCREENING AND TREATMENT WITH USP4 INHIBITORS

CROSS-REFERENCE TO RELATED APPLICATIONS

This application is a National Stage Application of PCT/GB2016/050517 filed Feb. 29, 2016, which claims priority from UK Patent Application No. 1503371.5, filed on Feb. 27, 2015. The priority of both said PCT and UK Patent Application are claimed. Each of prior mentioned applications is hereby incorporated by reference herein in its entirety.

FIELD

The present application relates to materials and methods for exploiting synthetic lethality and/or chemo-sensitisation in DNA damage response (DDR) pathways. In particular, the application relates to ubiquitin hydrolase protein Ubiquitin Specific Protease 4 (USP4) and its association with DDR pathways. Further, the use of USP4 inhibitors in the treatment of cancer and methods of screening is described, in particular, use of inhibitors of USP4 in the treatment of tumours defective in double-strand break repair (DSBR) and/or tumours resistant to platinum-based chemotherapy, or to sensitise, i.e. chemosensitise or radiosensitise tumours to other therapeutic agents. Screening or selection of patients on the basis of their DDR pathway status, particularly their BRCA2, XRCC4, Ligase IV or ATR status is also described.

BACKGROUND

DDR refers to a range of processes by which cells sense, signal and correct damage to genetic material. DNA damage has numerous sources such as chemotherapy, radiotherapy, UV light, replication errors and alkylating agents resulting in millions of lesions to the human genome every day. DNA repair processes continually keep the genome protected against the impact of propagating lesions that can have deleterious consequences. During tumourigenesis, genomic instability leads to mutations in key regulatory proteins including those involved in DDR/DNA repair, causing cells to become reliant on remaining DNA repair pathways. This reliance is known to vary between tumour types.

The concept of synthetic lethality was first derived from genetic studies in model organisms, where mutation of a particular gene results in lethality only through mutation or loss of another gene. The application of synthetic lethality to cancer biology has led to the discovery of novel therapeutic avenues to treat cancer. For instance, targeting DDR pathways that tumours have become reliant on has led to new approaches to selectively kill cancer cells with little toxicity to normal cells. In recent years, more rational approaches have been undertaken that are supported by the increased understanding of the type of pathways that are differentially defective in cancer versus normal cells (Nijman S M B and Friends S H, Science, 809-811).

The synthetic lethality approach to the treatment of cancer offers the possibility of selectively killing cancer cells by targeting pathways that the cell exclusively relies on for survival. This approach offers a significant advantage over cytotoxic chemotherapy and radiotherapy, and potentially represents a safer and more targeted treatment. However the characterisation of the specific dependencies based on this approach requires further understanding to enable the development of effective drugs useful in targeted cancer therapy.

The mouse USP4 orthologue was previously called the Unp gene. The USP4 gene maps to human chromosome 3p21.31. As ubiquitylation has been linked to regulation of cellular processes including protein homeostasis, transcription, and DNA repair, the inventors performed a cellular screen looking for synthetic lethality between USP4 and cell lines deficient in DDR proteins. They have identified that knockdown of USP4 resulted in synthetic lethality in cell lines depleted in DDR pathway proteins, particularly ATR, BRCA2, XRCC4 and Ligase IV. In addition, they found that depletion of USP4 was synthetic lethal in tumour cells resistant to treatment, such as cisplatin resistant cells compared to the parental control.

SUMMARY

According to a first aspect of the present invention there is provided a USP4 inhibitor for use in the treatment of cancer, wherein the cancer comprises cells deficient in one or more DNA damage response (DDR) pathways and/or cells resistant to platinum-based chemotherapy.

Thus, the use of USP4 inhibitor can enable treatment of relevant cancer cells without the requirement for further or additional anti-cancer agents. The USP4 inhibitor will selectively kill cancer cells, due to the synthetic lethal pairing of the DDR pathway deficiency or resistance to platinum-based chemotherapy. In such a synthetic-lethal pairing, normal (non-cancerous) cells are spared from the effects of the USP4 inhibitor.

According to a further aspect of the invention there is provided a method of screening for agents of USP4 suitable for use in the treatment of cancer, wherein the cancer comprises cells deficient in one or more DNA damage response (DDR) pathways and/or cells resistant to platinum-based chemotherapy.

In one embodiment, the cells are deficient in BRCA2, XRCC4, Ligase IV or ATR.

In a further embodiment, the cells are exposed to a putative inhibitor and cell viability is measured.

According to a further aspect of the invention, there is provided a use of cells with defective BRCA2, XRCC4, Ligase IV or ATR and/or cells resistant to platinum-based chemotherapy, for the screening of agents as inhibitors of USP4.

According to a further aspect of the invention there is provided a method of determining the responsiveness of a subject having a cancer to a USP4 inhibitor, the method comprising determining whether the cancer comprises cells deficient in one or more DNA damage response (DDR) pathways and/or cells resistant to platinum-based chemotherapy, wherein the presence of said deficiency or resistance in said cells indicates that the subject is responsive to a USP4 inhibitor.

Thus, a subject may be screened to determine whether therapy with a USP4 inhibitor will be effective and/or appropriate.

According to a further aspect of the invention there is provided a method of selecting subjects having a cancer for treatment with a USP4 inhibitor, the method comprising determining whether the cancer comprises cells with defective BRCA2, XRCC4, Ligase IV or ATR, or the cancer comprises cells resistant to platinum-based chemotherapy, and selecting said subjects showing defective BRCA2, XRCC4, Ligase IV or ATR in said cells or showing resistance to one or more platinum-based chemotherapies for treatment.

According to a further aspect of the invention, there is provided a method of overcoming resistance to one or more platinum-based chemotherapies in a subject treated with said chemotherapies, comprising determining the growth of one or more tumours or the relapse of a haematological cancer in said subject, and further treating the subject with an inhibitor of USP4.

According to a further aspect of the invention there is provided a method of treating a subject having a cancer comprising cells with defective BRCA2, XRCC4, Ligase IV or ATR, and/or said cancer comprises cells resistant to one or more platinum based chemotherapies, the method comprising administering to the subject a therapeutically effective amount of a USP4 inhibitor.

According to a further aspect, there is provided a use of the presence of a mutated BRCA2 gene, mutated BRCA2 protein, mutated XRCC4 gene, mutated XRCC4 protein, mutated LIG4 gene, mutated Ligase IV protein, mutated ATR gene or mutated ATR protein in a sample of cancer cells, as a biomarker for determining the sensitivity of said cancer to treatment with a USP4 inhibitor.

Optionally, the biomarker can determine the sensitivity of said cancer to treatment with a USP4 inhibitor.

According to a further aspect of the invention there is provided a method of treating a subject having a cancer comprising cells deficient in one or more DNA damage response (DDR) pathways and/or cells resistant to platinum-based chemotherapy, the method comprising administering to the subject a therapeutically effective amount of a USP4 inhibitor.

According to a further aspect of the invention there is provided a method of treating a subject having a cancer, the method comprising administering to the subject a therapeutically effective amount of a USP4 inhibitor in combination with one or more other anti-tumour therapeutic agents.

Thus, the use of a USP4 inhibitor can sensitise a tumour cell to treatment with another anti-tumour therapeutic agent. This may be sensitising for a chemical anti-tumour therapeutic agent or sensitising for a radiation-based anti-tumour therapeutic agent.

According to a further aspect of the invention there is provided a pharmaceutical composition comprising an agent for use in the treatment of cancer, wherein the cancer comprises cells deficient in one or more DNA damage (DDR) pathways and/or cells resistant to platinum-based chemotherapy, wherein said agent is a USP4 inhibitor.

According to a further aspect of the invention, there is provided a pharmaceutical composition comprising an agent for use in the treatment of cancer and a USP4 inhibitor. Said agent for use in the treatment of cancer may be any anti-tumour therapeutic agent.

Optional features are specified in the dependent claims. Further advantages are described below.

BRIEF DESCRIPTION OF THE FIGURES

Certain embodiments of the present invention will now be described, by way of example only, with reference to the drawings in which:

FIG. 12a is a graph showing USP4 promotes RAD51 loading and homologous recombination. Control (Luc or BRCA1) or USP4 (4 UTR) depleted cells were exposed to 5 Gy IR and left to recover for 8 hours, followed by immunofluorescent staining with antibodies against RAD51 and γH2AX. γH2AX positive cells containing more than 3 RAD51 foci were scored positive (mean±s.e.m., n=3). (**P<0.01).

FIG. 12b is a graph showing USP4 promotes RAD51 loading and homologous recombination. I-SceI induced genomic DSB repair assay in DR-GFP U2OS cells treated with control (Luc or CtIP) or USP4 (4-4, 4 UTR) siRNAs. Relative HR repair efficiencies were normalized to the Luc control (mean±s.e.m., n=4). (*P<0.05, **P<0.01).

FIG. 13 is a graph showing USP4 promotes non-homologous end-joining. Random plasmid integration assay in control (Luc or Lig IV) or USP4 (4-4 or 4 UTR) depleted U2OS cells to assess NHEJ repair efficiency. The relative NHEJ repair efficiencies were normalized to the control (Luc) which was set to a 100% (mean±s.e.m., n=3). (*P<0.05, **P<0.01).

FIG. 14 provides an image of purified FLAG-USP4 expressed in HEK-293 cells. FLAG-purified protein (5 μl) was separated by SDS-PAGE and stained with Imperial blue (Pierce Biotechnology).

DETAILED DESCRIPTION OF CERTAIN EMBODIMENTS

Figure 1:
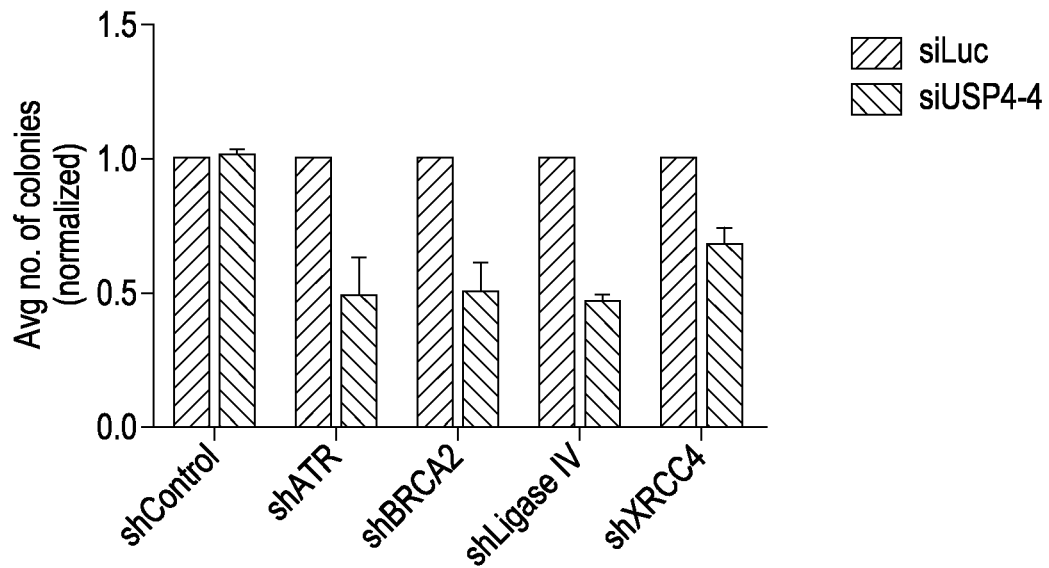
FIG. 1 is a graph showing selective killing of DDR-deficient cells compared to isogenic DDR-wild-type-cells, via a colony-forming assay. Control or DDR-deficient HeLa cervical carcinoma cells were transfected with control (si-Luc) or USP4-specific siRNA (siUSP4-4) for 24 h before re-seeding into multi-well plates. The cells were incubated for 12 days before the colonies were fixed in Giemsa stain and counted. Average of three experiments is depicted, error bars represent SEM. This data supports the assertion that siUSP4 is synthetic lethal with DDR deficient cells.

In the Examples, it is shown that DDR pathways which have not previously been associated with USP4 function are determined and the results show that inhibition of USP4 is an effective strategy for the treatment of tumours deficient in DDR pathways. In particular, it has been demonstrated that USP4 compensates for deficiencies or defects in BRCA2, Ligase IV, XRCC4 and ATR proteins as shown in the Examples. USP4 is thus essential for cell survival in cancers having a deficiency in one or more of these proteins and associated DDR pathways. This has significance in the development of USP4 inhibitors which have use in the treatment of tumours characterised by a deficiency in one or more of these pathways and provides for the pre-screening of patients to identify those who would benefit from USP4 inhibitor treatment.

The Examples demonstrate that inhibition of USP4 is effective in selectively killing cancer cells that are resistant to platinum-based chemotherapy treatment. In particular the results demonstrate that USP4 inhibition preferentially kills cancer cells which are resistant to platinum-based treatment. These findings have significance and potential in the development of new drugs and treatment regimens for patients that have developed resistance to platinum-based chemotherapy.

According to an aspect of the invention there is provided a USP4 inhibitor for use in the treatment of cancer, wherein the cancer comprises cells deficient in one or more DNA damage response (DDR) pathways.

According to an aspect of the invention there is provided a USP4 inhibitor for use in the treatment of cancer, wherein the cancer comprises cells resistant to platinum-based chemotherapy.

In another aspect there is provided use of a USP4 inhibitor in the manufacture of a medicament for the treatment of cancer, wherein the cancer comprises cells deficient in one or more DNA damage response (DDR) pathways.

In another aspect there is provided use of a USP4 inhibitor in the manufacture of a medicament for the treatment of cancer, wherein the cancer comprises cells resistant to platinum-based chemotherapy.

USP4 is ubiquitin-specific protease 4 polypeptide, and may include variants, mutants and fragments thereof. USP4 is a member of the ubiquitin-specific processing protease superfamily and functions as a deubiquitylating enzyme by removal of the ubiquitin moiety from ubiquitin-conjugated precursors and ubiquitinylated proteins. USP4 was previously named UNP, prior to standardization of the nomenclature.

The USP4 polypeptide may be in its native or wild type form which refers to a USP4 polypeptide having an amino acid sequence corresponding to that found in nature.

Alternatively the USP4 polypeptide may be a variant having at least 80%, 90% or 95% sequence amino acid identity to the native amino acid sequence. The protein sequence of human USP4 is provided in SEQ ID NO: 1, and the mRNA sequence of human USP4 is provided as SEQ ID NO: 2.

USP4 may be derived from any source, for example a eukaryotic source or a prokaryotic source. In an embodiment USP4 is mammalian and derived from rat, mouse, rabbit, dog, or non-human primate. In an embodiment USP4 is avian and derived from chicken or turkey. In an embodiment USP4 is human. In a further embodiment USP4 may be derived from human tissues or from recombinant synthetic methods.

The USP4 polypeptide may be a mutant polypeptide with a different genotype to the wild type or native form of USP4. Such a mutant may also result in a different phenotypic difference. Mutants of USP4 may be produced by any suitable method where each amino acid of the native USP4 protein is independently changed to a different amino acid residue. Molecular biological techniques for cloning and engineering genes and cDNAs, for mutating DNA, and for expressing polypeptides from polynucleotides in host cells are well known in the art as exemplified "Molecular cloning, a laboratory manual", third edition, Sambrook, J. & Russell, D. W. (eds), Cold Spring Harbor Laboratory press, Cold Spring Harbor, N.Y., incorporated herein by reference.

For the avoidance of doubt, "derived from" means that the cDNA or gene was originally obtained from the defined source and the USP4 protein may be expressed in any suitable host cell. For example USP4 derived from a eukaryotic source may be expressed in a prokaryotic host cell such as *E. coli*.

Deubiquitylating activity is the catalytic or enzymatic activity of USP4 and the removal of ubiquitin from proteins such as k63-linked ubiquitin conjugates from TRAF2, TRAF6 and TAK1. Other known substrates or interaction partners of USP4 include TRIM21, RIG-1, RIP 1, PDK1, pRb (retinoblastoma tumour suppressor), pocket proteins p107 and p130, ARF-BP1, TGFβ Receptor I, PDK1 kinase, Ros52, the spliceosomal protein Prp19, S9/Rpn6 subunit of the proteasome and A2a adenosine receptor.

USP4 inhibitors may be an agent capable of binding to or interacting with USP4 and causing a reduction in functional activity of USP4, for example a decrease in catalytic or enzymatic activity which may be partial or complete. The inhibitor may interact with the active site of USP4 or interact with another site on USP4 and act as an allosteric inhibitor. Any agent that causes a reduction in the functional activity of USP4 is considered to be an inhibitor.

Partial or complete reduction in the functional activity of USP4 may cause cell death or apoptosis of cancer cells which are defective in one or more DDR pathways and are reliant or hyper-dependent on USP4 mediated repair, thus allowing selective targeting and killing of cancer cells whilst normal (non-cancerous) replicating cells survive.

A USP4 inhibitor may be a known USP4 inhibitor, a polypeptide, polynucleotide, antibody, peptide, small molecule compound, an RNA-based drug (included but not limited to short interfering RNA (siRNA), short hairpin RNA (shRNA) and/or microRNA (miRNA)) molecule or any other suitable chemical. In one embodiment a USP4 inhibitor is an RNA molecule that functions as an inhibitory RNA molecule or a small molecule compound. RNA levels may also be modulated by introduction of a miRNA. RNA and DNA molecules may also form aptamers. In one embodiment a USP4 inhibitor is an RNA-based drug, such as an inhibitory (RNAi) molecule, or a small molecule compound.

The USP4 inhibitors may be specific or selective for USP4.

References to "antibody" include but are not limited to monoclonal, human, humanized or chimaeric antibodies. The antibody may be an antibody fragment or derivative thereof including a VH or VL domain, a single chain antibody molecule (scFv), an antigen-binding fragment (Fab) or a "third generation" fragment (3G—miniaturised antibodies derived from full sized antibodies by removing domains deemed to be non-essential). In one embodiment the antibody is human, but in other embodiments the antibody may be from an animal or humanized References to "RNA interference (RNAi)" refer to a technique used to "knock down" gene function through the introduction of double stranded RNA (RNAi) into the cell resulting in the inhibition of mRNA complementary to one of the RNAi sequences. This can be achieved by a variety of RNA molecule types including siRNA, shRNA and miRNA.

Known USP4 inhibitors and derivatives thereof, such as Vialinin A, a small compound isolated from the Chinese mushroom *Thelephora vialis* (as described in Okada K et al., Bioorg Med Chem Lett, 2013, Aug. 1; 23(15) 4328-31.) are of use according to the present invention and are incorporated herein.

Patients/subjects may be screened or selected for treatment with a USP4 inhibitor on the basis of their USP4 status. For example, the level of expression of USP4 or if USP4 is defective may be determined. Standard methods may be used to determine the expression and nature of the USP4, such as those described below for the other DDR pathway components.

DNA damage response (DDR) pathways are a range of processes by which cells sense, signal and correct damage to genetic material. DNA damage can be caused by chemotherapy, radiotherapy, UV light, replication errors and alkylating agents, for example.

Cells deficient in one or more DNA damage response (DDR) pathways may have one or more DDR pathways that are dysfunctional or defective such that normal function is impaired either partially or completely.

The DDR pathways may be selected from one or more of, base excision repair (BER), single strand break repair, mismatch repair, nucleotide excision repair (NER), transcription-coupled repair, non-homologous end joining repair, translesion synthesis and double strand break repair processes, including homologous recombination repair; double strand break (DSB) signalling and DNA inter-strand cross-link repair (including the Fanconi Anaemia pathway).

Deficiencies in DDR pathways may be due to mutations in, the absence of or defective expression of a gene encoding a protein involved in homologous recombinational repair, base excision repair, single strand break repair, mismatch repair, nucleotide excision repair, transcription-coupled repair, non-homologous end joining repair, translesion synthesis or DNA inter-strand cross-link repair.

In an embodiment the DDR pathway that is deficient is involved in the repair of double-strand breaks. In particular, the cells may be deficient in one or more DDR pathways selected from homologous recombinational (HR) repair or non-homologous end-joining (NHEJ) repair.

In certain embodiment deficiencies in DDR pathways are due to mutations in, the absence of, or defective expression of a gene encoding proteins selected from one or more of ATR, BRCA2, Ligase IV and XRCC4.

In certain embodiment cells deficient in one or more DDR pathways have increased sensitivity to DNA damaging agents such as chemotherapeutic agents.

Reference to "ATR" refers to the Ataxia-Telangiectasia and Rad3-related which is a serine/threonine protein kinase belonging to the PI3KK subfamily of kinases (PI3K-related kinases) that is recruited and activated by the persistent presence of single stranded DNA indicating DNA damage, such as single-strand DNA damage, replication fork defects and maintenance of fragile site in the genome. Single stranded DNA is an intermediate in several DDR pathways, including but not limited to nucleotide excision repair, mismatch repair, base excision repair and homologous recombination. This kinase has been shown to phosphorylate checkpoint kinase CHK1, checkpoint proteins RAD17, and RAD5, as well as tumour suppressor protein BRCA1. Mutations of this gene are associated with Seckel syndrome.

"BRCA2" denotes breast cancer type 2 susceptibility protein. Carriers of heterozygous germ-line mutations in the BRCA1 or BRCA2 genes are strongly predisposed to cancer of the breast, ovary, and other organs. BRCA1 and BRCA2 proteins are critically important for the repair of double strand breaks by homologous recombination and loss of the wild-type BRCA1 or BRCA2 allele in tumours likely fosters cancer progression by promoting genome instability and mutation.

"Ligase IV" or "Lig IV" denotes DNA Ligase IV, an ATP-dependent DNA ligase that joins double-strand breaks during the non-homologous end-joining (NHEJ) pathway to repair DNA double strand breaks. This protein forms a complex with the X-ray repair cross complementing protein 4 (XRCC4), and further interacts with the DNA-dependent protein kinase (DNA-PK). Defects in this gene are the cause of LIG4 syndrome, with symptoms such as acute radiosensitivity, immunodeficiency and bone marrow abnormalities.

"XRCC4" denotes X-ray repair cross complementing protein 4. This is one of several core proteins involved in the NHEJ pathway to repair DNA double strand breaks. This protein forms a complex with Ligase IV as discussed above. The non-homologous end-joining pathway is required both for normal development and for suppression of tumours. XRCC4 polymorphisms have been linked to a risk of susceptibility for cancers such as bladder cancer, breast cancer, prostate cancer, hepatocellular carcinoma, lymphomas, and multiple myeloma.

Tumour cells that do not effectively respond to treatment with one or more platinum-based chemotherapeutics may be described as resistant to platinum-based chemotherapy. Such cells have either intrinsic or acquired cellular mechanisms that allow continued survival in the presence of platinum chemotherapeutic agents compared to tumour cells sensitive to platinum chemotherapeutic agents and as such a higher dose is required to effect cell killing.

Tumours cells that are refractory to platinum-based treatment i.e. do not show even a partial response to platinum-based chemotherapy or that initially respond to platinum-based chemotherapy but then recur within a short time following completion of the treatment may also be defined as resistant. Such cells are likely to have either intrinsic or acquired cellular mechanisms that allow continued survival in the presence of platinum based chemotherapeutic agents, and as such, as higher dose may be required in order to effect cell killing. The recurrence of cancer cells after treatment may be immediate or recur within a short time. This time may be defined differently for various tumour types but for ovarian cancer this time has been determined by the Gynaecologic Oncology Group as a period of 6 months. Thus, a cancer that recurs within 6 months is likely to be resistant to platinum-based drugs.

Resistance to platinum-based chemotherapy occurs in a wide range of cancers, including but not limited to lung, ovarian, bladder, colorectal, oesophageal, head and neck, testicular, breast, cervix and gastric cancers.

Platinum-based chemotherapy agents/treatments are known to those skilled in the art and include, for example carboplatin, cisplatin, oxaliplatin, picoplatin, nedaplatin, triplatin and satraplatin.

Furthermore it is recognised that inhibition of USP4 may selectively kill tumour cells with reduced activity of double-strand break repair proteins by further reducing the levels of these activities.

Cancer cells having mutations in, the absence of or defective expression of a gene encoding a protein involved in double-strand break repair processes are selectively killed in the presence of USP4 inhibition. FIGS. 9a to 9f, 11a to 11d, 12a to 12b, and 13 clearly show that USP4 promotes repair of double-strand breaks.

DNA double-strand breaks (DSBs) are deleterious forms of DNA damage that may result in rearrangement or loss of genomic material, ultimately leading to cell death or carcinogenesis. DSBs may be induced by ionizing radiation (IR), but they also occur during normal endogenous processes including DNA replication, and V(D)J recombination.

The Examples demonstrate that cancer cells deficient in ATR, BRCA2, Ligase IV and XRCC4, or cells resistant to platinum-based chemotherapy are selectively killed in the presence of USP4 inhibition. Thus, tumours with reduced ATR, BRCA2, Ligase IV and XRCC4, or resistant to platinum based chemotherapy are hyper-dependent on USP4.

In a further embodiment there is provided a USP4 inhibitor for use in the treatment of cancer, wherein the cancer comprises cells resistant to platinum-based chemotherapy, or cells deficient in one or more DNA damage response (DDR) pathways, wherein such deficiencies are due to mutations in, the absence of or defective expression of a gene encoding proteins selected from one or more of ATR, BRCA2, Ligase IV and XRCC4.

In an embodiment there is provided a USP4 inhibitor for use in the treatment of cancer, the cancer comprising cells resistant to platinum-based chemotherapy, or cells deficient in one or more DNA damage response (DDR) pathways wherein cells resistant to platinum-based chemotherapy, or cells deficient in one or more DNA damage response (DDR) pathways are hyper-dependent on USP4 associated pathways for survival.

In an aspect of the invention, a USP4 inhibitor may be combined with one or more additional anti-tumour therapeutic agents, for example, radiation or chemotherapeutic drugs or inhibitors of other regulatory proteins/other DNA damage response proteins. This combined treatment may be applied to a subject having cancer. The inventors have also identified combination therapies for USP4 inhibitors with anti-tumour therapies, as shown in the Examples and the Figures. Thus, the use of a USP4 inhibitor can sensitise a cancer cell to treatment with another anti-tumour therapy. This may be sensitising for a chemical anti-tumour agent or for a radiation-based anti-tumour agent. In the embodiment, the cancer cell does not need to have a defect in DDR pathways.

It will be understood that the combination does not need to be a physical combination, but a combined therapy, where the USP4 inhibitor and anti-tumour therapeutic agent are applied separately or sequentially.

Any suitable combination may be used of USP4 inhibitor and an additional anti-tumour therapeutic agent.

In this aspect of the invention, the USP4 inhibitor is thought to be acting as a sensitising agent, i.e. chemosensitising or radiosensitising agent, priming cancer cells for killing with the use of one or more additional or further anti-tumour therapeutic agent.

The anti-tumour therapeutic agent may be any agent suitable for treating a tumour or cancer.

The additional anti-tumour therapeutic agent may be selected from an ATR inhibitor, a BRCA2 inhibitor, a Ligase IV inhibitor and a XRCC4 inhibitor. In one embodiment the ATR inhibitor may be selected from one or more of AZD6738 and VE-822. In an embodiment, the inhibitor of XRCC4 may be selected from one or more of S-(Dimethylarsenic)Cysteine, Myricetin and some xanthone series (Sun et al, J Biomol Struct Dyn (2011) 29(2):325-37). In an embodiment, the Ligase IV inhibitor may be selected from SCR7 (Srivastava et al, Cell (2012) 151(7): 1474-87) or L189 (Chen et al, Cancer Res (2008) 68(9):3169-77).

The USP4 inhibitor may be combined with ionising radiation and/or the following chemotherapeutic agents: platinums, PARP inhibitors, cross-linking agents, topoisomerase I chemotherapeutic agents, topoisomerase II chemotherapeutic agents, alkylating agents and radiomimetics. Ionising radiation and the chemotherapeutic agents are thus additional anti-tumour therapeutic agents according to the present invention.

The USP4 inhibitor may be combined with a PARP (poly ADP ribose polymerase) inhibitor, which may be an inhibitory RNA (RNAi) molecule (PARPi). In a further embodiment PARP inhibitors may be selected from one or more of Iniparib (BSI 201), Olaparib (AZD-2281), Rucaparib (AG014699, PF-01367338) and Veliparib (ABT-888), MK-4827, CEP-9722, E7016(GPI-21016), LT-673, MP-124, NMS-P118. PARP denotes Poly-(ADP-ribose) polymerase enzymes that play a role in the repair of single stranded DNA (ssDNA) breaks. The PARP family comprises 17 members, all thought to have a role in DNA repair and cell death. PARP-1 and PARP-2 are both activated by DNA single stranded breaks.

The additional anti-tumour therapeutic agent may be a platinum-based chemotherapy. Suitable platinum based chemotherapies include: carboplatin, cisplatin, oxaliplatin, picoplatin, nedaplatin, triplatin and satraplatin.

The additional anti-tumour therapeutic agent may be a cross-linking agent. Suitable cross-linking reagents include cisplatin, Mitomyocin C, Melphalan and cyclophosphamide.

The USP4 inhibitor may be combined with an additional anti-tumour therapeutic agent that is a topoisomerase I chemotherapeutic agent or a topoisomerase II chemotherapeutic agent. Chemotherapeutic agents may include poisons and inhibitors of toposimerase I and/or II. Poisons may be a compound that targets the topoisomerase-DNA complex, rather than inhibits the topoisomerase. Suitable topoisomerase I chemotherapeutic agents include camptothecin, irinotecan, topotecan and lamellarin D. Suitable topoisomerase II chemotherapeutic agents include etoposide (VP-16), teniposide, doxorubicin, daunorubicin, mitoxanthine, amsacrine, ellipticines, aurintricarboxylic acid and HV-331.

The additional anti-tumour therapeutic agent may be an alkylating agent. Suitable alkylating agents include bendamorphine, busulfan, chlorambucil, carboplatin, cisplatin, oxaliplatin, isofamide, temozolomide and cyclophosphamide.

The additional anti-tumour therapeutic agent may be a radiomimetic. Suitable radiomimetics include bleomycin, dactinomycin and streptonigrin.

The additional anti-tumour therapeutic agent may be a spindle poison or anti-mitotic. Suitable spindle poisons include taxanes (including paclitaxel) mebendazole, colchicine, griseofulvin, and vinca alkaloids.

The additional anti-tumour therapeutic agent may be an anti-metabolic agent. Suitable anti-metabolic agents include fluropyrimidines, azathioprine and mercaptopurine.

The additional anti-tumour therapeutic agent may be a nucleoside analogue or nucleobase analogue. Suitable analogues include vidarabine, cytarabine and gemcitabine.

In certain embodiments, the additional anti-tumour therapeutic agent is selected from the list comprising ionizing radiation (IR) or a chemotherapeutic agent selected from bleomycin, etoposide, carboplatin, camptothecin, or olaparib, or a combination thereof.

Cancer or tumours may include but are not limited to breast, ovarian, prostate, lung, kidney, gastric, colon, testicular, head and neck, pancreatic, brain, melanoma, oesophageal, bladder, cervical, endometrial, bone or other cancers of tissue organs, and cancers of the blood cells such as lymphomas and leukaemias.

It will be understood by the skilled person that if USP4 is used in combination with another/additional anti-tumour therapeutic agent as described herein, that the combination may be applied to the subject at the same time, simultaneously, sequentially or separately. Each of the USP4 inhibitor and additional anti-tumour therapeutic agent may be administered by a different route, for example. Routes of administration are discussed further below and apply equally to the USP4 inhibitor and the additional anti-tumour therapeutic agent.

The USP4 inhibitor and additional anti-tumour therapeutic agent may be used in a subject whose cancer comprises cells that are deficient in one or more DDR pathways or the cancer comprises cells that are resistant to a platinum-based chemotherapy.

As demonstrated in the Examples, combination therapies have been identified for USP4 inhibitors with ionising radiation or the following chemotherapeutic agents: platinums, PARP inhibitors, cross-linking agents, topoisomerase I chemotherapeutic agents, topoisomerase II chemotherapeutic agents, alkylating agents and radiomimetics.

The use of USP4 inhibitors in conjunction with an additional anti-tumour therapeutic agent offers an advantage over conventional chemotherapy treatment allowing the selective targeting of cancer cells thereby reducing the side effects known to be associated with chemotherapeutic drugs.

In an embodiment USP4 inhibitors are useful in the treatment of cancer, wherein the cancer is at least partially responsive to treatment with an anti-cancer agent. For example the anti-cancer agent may be ionizing radiation (IR) or a chemotherapeutic agent selected from a PARP inhibitor (e.g. olaparib), a topoisomerase I or II chemotherapeutic agent (e.g. camptothecin or etoposide), a platinum-based chemotherapeutic agent such as (e.g. cisplatin), cross-linking agents (e.g. mitomyocin C), alkylating agents (e.g. isofamide) and/or radiomimetics (e.g. bleomycin). It is preferred that the USP4 inhibitor is used in combination with another anti-tumour therapeutic agent to treat such cancers.

According to a further aspect of the invention there is provided a method of screening for inhibitors of USP4 suitable for use in the treatment of cancer, wherein the cancer comprises cells deficient in one or more DNA damage response (DDR) pathways or cells resistant to platinum-based chemotherapy.

Inhibitors of USP4 have been discussed previously and may be agents that reduce the activity of USP4, including antagonists or inverse agonists of USP4 Examples include a polypeptide, polynucleotide, antibody, aptamers, peptide, small molecule compound, an RNA-based drug (included but not limited to short interfering RNA (siRNA), short hairpin RNA (shRNA) and/or microRNA (miRNA)) molecule or any other suitable chemical. The reduction may be partial or complete. Agents that function such that the intrinsic activity of USP4 is not affected but the ability of USP4 to bind to its substrate or co-factor is impaired are also included in the scope of any aspect of the invention.

USP4 may be isolated for screening by any conventional means, including the method described in "Short protocols in molecular biology" Ausubel et al, Wiley, Fourth Edition, 1999.

The method of screening may comprise the steps of:
a) Obtaining purified or recombinant USP4 complex from mammalian cells
b) Contacting the isolated USP4 with one or more test agents and the appropriate substrate for USP4
c) Selecting those agents that demonstrate a reduction in USP4 activity.

In one embodiment the agent identified in step c) has a binding affinity in the nanomolar (nM) or micromolar (µM) range. In another embodiment the agent demonstrates specific binding to USP4 such that binding to other proteins is significantly reduced or absent.

In particular, the appropriate substrate for USP4 is TAMRA labelled peptide linked to ubiquitin via an isopeptide bond as fluorescence polarization substrate.

Further methods used to identify inhibitors of purified or recombinant USP4 will be appreciated by those skilled in the art. In certain embodiments the reduction in USP4 is a reduction in catalytic activity.

According to a further aspect of the invention there is provided a method of screening for inhibitors of USP4 using isogenic pairs of cell lines proficient and deficient in one or more DNA damage response (DDR) pathways or cells resistant to platinum-based chemotherapy. USP4 inhibitors will be more potent in deficient or resistant cells versus proficient or sensitive cells.

A reduction in activity of USP4 may be measured in vitro by a reduction in cell proliferation of cells deficient in at least one DDR pathway. In certain embodiments the reduction in cell proliferation is due to cell cycle arrest or apoptosis. In certain embodiments a reduction in catalytic activity of USP4 is measured in vitro by a reduction in the deubiquitylating activity of USP4.

Inhibition of catalytic activity of USP4 may be measured using in vitro techniques, including the method described in Tirat et al, (Anal Biochem 343 (2005) 244-255).

Test agents may be small molecules, peptides, polypeptides, polynucleotides, aptamers, oligonucleotides, RNA molecules as described previously, antibodies or libraries thereof.

According to a further aspect of the invention there is provided a method of determining the responsiveness of a subject having a cancer to a USP4 inhibitor, the method comprising determining whether the cancer comprises cells deficient in one or more DNA damage response (DDR) pathways, or cells resistant to platinum based chemotherapy wherein the presence of said deficiency or said resistance indicates that the subject is responsive to a USP4 inhibitor. In one embodiment, the DDR pathways are involved in double-strand break repair, particularly non-homologous end joining (NHEJ) and Homologous recombination (HR).

Optionally, any of the methods of the invention, such as determining the responsiveness of a subject, or selecting a subject, may further comprise determining whether the non-cancer (normal) cells of the subject comprise cells which are deficient in said DDR pathways. The normal cells and the cancer cells of the subject may be compared to determine if the cancer cells are deficient in one or more DDR pathways relative to the normal cells. It may be preferred in some instances that the cancer cells are deficient in one or more DDR pathways, and the normal cells are not deficient in said pathways. Optionally it may be that the normal cells are heterozygous for a mutation in a DDR pathway gene or carry a polymorphism in a DDR pathway gene, whilst not being deficient in said pathways.

The Examples have demonstrated that deficiencies in one or more of DNA damage response proteins ATR, BRCA2, Ligase IV and XRCC4 in cancer cells, or resistance to platinum based chemotherapy results in selective killing of cells where USP4 is silenced. Therefore the absence of functional ATR, BRCA2, Ligase IV and XRCC4 proteins in cancer cells, or resistance to platinum based chemotherapy represent useful biomarkers that can be used to select or screen for patients that would benefit from USP4 inhibitor treatment. Screening of cancer patients suitable for USP4 inhibitor treatment has the advantage that treatment in patients who have an absence of deficiencies in the DNA damage response proteins described above is avoided, thus ensuring relevant patient populations are targeted. It further ensures that patients who have become resistant to previously effective platinum-based chemotherapy have a further treatment option.

In certain embodiments the responsiveness of a subject to a USP4 inhibitor is determined by the absence in cancer cells of one or more biomarkers selected from ATR, BRCA2, Ligase IV and XRCC4 functional proteins. In certain embodiments the responsiveness of a subject to a USP4 inhibitor is determined by the presence of one or more amino acid or nucleic acid mutations in the sequence of the genes encoding ATR, BRCA2, Ligase IV and XRCC4 in cancer cells. The responsiveness of a subject to a USP4 inhibitor may be determined by measuring the levels of ATR, BRCA2, Ligase IV and XRCC4 mRNA in cancer cells, wherein abnormally low levels indicate that the subject is responsive to a USP4 inhibitor.

According to a further aspect, there is provided the use of the presence of a mutated BRCA2 gene, mutated BRCA2 protein, mutated ATR gene, mutated ATR protein, mutated LIG4 gene, mutated Ligase IV protein, mutated XRCC4 gene or mutated XRCC4 protein in a sample of cancer cells as a biomarker for determining the sensitivity of said cancer with treatment with a USP4 inhibitor.

The sample of cancer cells may be taken according to any standard practice, including biopsy.

In an embodiment, the biomarker can determine the sensitivity of said cancer to treatment with a USP4 inhibitor alone or in combination with a further anti-tumour therapeutic agent.

In one embodiment the method further comprises identifying the responsiveness of a cancer cell to a USP4 inhibitor, wherein the presence of said deficiency indicates that the cancer cell is responsive to a USP4 inhibitor.

In certain embodiments the cancer cell has defective BRCA2, XRCC4, Ligase IV or ATR or a combination thereof. The defect may be in the BRCA2, XRCC4, LIG4 or ATR gene, expression of the BRCA2, XRCC4, LIG4 or ATR gene or in the BRCA2, XRCC4, Ligase IV or ATR protein, such as post-translational modifications.

Thus, the defective BRCA2, XRCC4, Ligase IV or ATR may be due to mutations in, the absence of, or defective expression of the genes encoding these proteins. Defective BRCA2, XRCC4, LIG4 or ATR genes or expression thereof may be mutated, absent or deficient. It has been found that defective BRCA2, XRCC4, Ligase IV or ATR are useful biomarkers which are each individually predictive of the sensitivity of cancer cells to treatment with a USP4 inhibitor. In particular, it has been found that the presence of a mutated BRCA2, XRCC4, LIG4 or ATR gene, deficient or absent BRCA2, XRCC4, Ligase IV or ATR protein correlates well with increased cell killing resulting from treatment with a USP4 inhibitor.

According to an aspect of the invention there is provided a method of determining the responsiveness of a subject having a cancer to a USP4 inhibitor, the method comprising determining whether the cancer comprises cells with defective BRCA2, XRCC4, Ligase IV or ATR wherein the presence of said defect indicates that the subject is responsive to a USP4 inhibitor. If the defect is present, the subject may be treated with a USP4 inhibitor.

The defect can be any defect in the BRCA2, XRCC4, LIG4 or ATR gene, the BRCA2, XRCC4, Ligase IV or ATR protein or the expression of the latter, such as those discussed above. Determining whether a cancer cell has a mutation in the nucleotides encoding BRCA2, XRCC4, Ligase IV or ATR protein can be performed in any suitable way.

Optionally, a sample of normal cells from the subject may also be tested. The normal cells can be analysed as described above, in order to determine whether the normal cells have any defect in the BRCA2, XRCC4, LIG4 or ATR gene, the BRCA2, XRCC4, Ligase IV or ATR protein or the expression of the latter, such as those discussed above. The normal cells and the cancer cells may be compared to determine whether any defect in the BRCA2, XRCC4, LIG4 or ATR gene, the BRCA2, XRCC4, Ligase IV or ATR protein or the expression of the latter is present only in the cancer cells. It may be that the normal cells are heterozygous for a mutation in a in the BRCA2, XRCC4, LIG4 or ATR gene or carry a polymorphism in the BRCA2, XRCC4, LIG4 or ATR gene, but are not deficient in said DDR pathway.

The BRCA2 gene is approximately 10,200 base pairs in length comprising 26 coding exons. The wild-type gene encodes a protein comprised of 3418 amino acids. Various mutations in BRCA2 have been associated with cancer. These include copy number abnormalities, deletion or duplication mutants, nonsense and frameshift mutations that prematurely truncate the protein, missense mutations and non-coding intervening sequence (IVS) mutations, deletions and duplications of entire or multiple exons, large genomic rearrangements, in frame deletions/duplications and sequence mutations, such as insertions, deletions or substitutions of nucleotides. Examples of polymorphisms, deletions and insertions known to be associated with an increased risk of cancer are c.5946delT, c.8363G>A, c.8754+1G>A, c.3860delA, c.7806-2A>G, c.8357_8538delAG, c.3170_3174de15, c.5857G>T, c2808_2811del4, c.6629_6630delAA, c.9026_9030del5, c.9310_9311delAA, c.5146_5149del4, c.156_157insAlu, c.516+1G>A, c.6275_6276delTT, c8904delC, c.5351dupA, c.6275_6276delTT, c.1813dupA, c.4478del4, c.9098dupA, c.7913_7917del5, c.8357_8538del2, c.9098dupA, c.5946delT, c.8755delG, c.6373delA, c.1310_1013del4, c.6486_6489del4, c.3847_3848delGT, c.4528delG, c.2808del4, c.3847delGT, c.7480C>T, c.8327T>G, c.9118-2A>G, c.9117+1G>A, c771_775del5, c.6275_6726delTT and c.1929delG (BRCA2 is numbered according to Genbank U43746 reference sequence). Any of these variations can be detected.

All mutations are named according to Human Genome Variation Society recommendations—http://www.hgvs.org/rec.html The mutation in ATR may be in any part of the nucleotide sequence for ATR, including non-coding or coding parts of the gene. The mutation may cause no ATR to be translated or allow for translation of a truncated or shortened version of ATR. Alternatively, the mutation in ATR may be a mutation of one or more nucleotides, insertions, deletions or replacements. A missense mutation resulting in a substituted amino acid residue c.6431A>G (p.Gln2144Arg) may be associated with oropharyngeal-cancer lesion (NCBI RefSeq accession number NM_001184.3). Other substituted amino acid residues associated with cancer are p.Glu2537Gln, p.Glu2438Lys, p.Ala1488Pro and p.Ala2002Gly. (Numbered according to GenBank accession number: U76308.1)

Polymorphisms in XRCC4 have been linked to a risk of susceptibility for cancers such as bladder cancer, breast cancer, prostate cancer, hepatocellular carcinoma, lymphomas, and multiple myeloma. Examples of such include polymorphisms rs2075686 (C>T) and rs6869366 (G-1394T) in the XRCC4 gene have been associated with increased risk of breast cancer. Missense variant rs3734091 (c.739G>T, p.Ala247Ser) is also associated with breast cancer. A deletion in intron 3 rs28360071 has been associated with oral cancer. Over 6,000 mutations or polymorphisms in XRCC4 have been reported, with some of these being linked to a risk of susceptibility to cancer.

Human XRCC4 gene sequence is available as Genbank accession number AH008055.1, which shows the alternative splice products. XRCC4 protein sequence is available as GenBank accession number: AAD47298.1.

Ligase IV defects may include a G to A mutational change at position 833 of the DNA ligase IV cDNA, which results in an arginine-to-histidine substitution at amino acid position 278 (R278H), which has been shown to be associated with leukaemia. Other exemplary mutations shown to be associated with cancers include rs10131, rs1805388, rs1805386 and rs4987182 (T1977C). Some 300 mutations or polymorphisms of the LIG4 gene are currently known.

DNA Ligase IV reference sequence is found under NG_007396.1, or GenBank: AF479264.1 (both nucleic acid and protein).

Single nucleotide polymorphisms or other mutations in these genes, may be found at http://www.ncbi.nlm.nih.gov/SNP/(NCBI dsSNP Short Genetic Variations database) and/or http://www.uniprot.org/docs/humsavar (UniProt Human polymorphisms and disease mutations database).

Determining whether a cell has defective DDR pathway components can be performed by any technical means. Said means may be on the basis of analysis for genetic changes, for example by examining DNA for nucleotide mutations, nucleotide additions or nucleotide deletions in the BRCA2, LIG4, ATR or XRCC4 gene. Additionally, DNA can be examined for larger-scale changes affecting these genes, including inversions, translations, translocations, loss of heterozygosity (LOH), deletions, and/or amplification. Alternatively, the cells can be examined for epigenetic changes, such as DNA methylation or chromatin restructuring, which may alter the expression of the genes. Further means to determine whether a cancer cell has defective BRCA2, ATR, Ligase IV or XRCC4 includes determination on the basis of RNA or mRNA expression from their respective genes. A further alternative means is on the basis of mutations in the polypeptide sequence compared to the wild-type sequence or modification of the protein, such as the presence or absence of post-translational modifications, i.e. glycosylation, phosphorylation or methylation. Such changes may be detected by standard techniques, including the use of antibodies specific for the mutation or post-translational modification. Alternatively, defective proteins can be detected on the basis of XRCC4, Ligase IV, ATR or BRCA2 protein expression, which can be established by standard techniques, such as Western blotting. It is possible to monitor blood samples from a subject for circulating DNA, mRNA or cells containing defective BRCA2, Ligase IV, XRCC4 or ATR using any of the techniques outlined herein. Immunohistochemistry may be used to visualise aberrant gene products. Furthermore, the cancer cells can be tested for functional DNA repair activity using any suitable assay. For example, the homologous recombination defect score (HRD) can be determined (such as the method described in Myriad Genetics, Abkevich et al, British Journal of Cancer (2012) 107, 1776-1782), Collins, A. R. (March 2004)). Alternative functional DNA repair assays include the Single Cell Gel Electrophoresis assay (SCGE, also known as the Comet assay) (Collins, A. R. (March 2004). Mol Biotechnol. 26 (3): 249-61) and Rad51 foci assays (Mukhopadhyay et al, Clin Cancer Res Apr. 15, 2010 16; 2344). Such assays may be used in clinical samples to assay DNA repair activity.

For example, nucleotide mutations may be detected by any DNA sequencing, i.e. using Real-Time PCR based assays, primer-extension assays, Sanger sequencing assays, or quantitative parallel pyrosequencing methods.

According to an aspect of the invention, there is provided a method of selecting subjects having a cancer for treatment with a USP4 inhibitor, the method comprising determining whether the cancer comprises cells with defective BRCA2, Ligase IV, XRCC4 or ATR and selecting said subjects showing defective BRCA2, Ligase IV, XRCC4 or ATR for treatment. Said method may involve determination of whether the cancer cell has defective BRCA2, Ligase IV, XRCC4 or ATR as defined above. Following selection, the patient may be treated with a USP4 inhibitor. Said method may optionally further involve determination of whether the normal (non-cancer) cells has defective BRCA2, Ligase IV, XRCC4 or ATR as defined above, or if the normal cells are heterozygous for a mutation in the BRCA2, XRCC4, LIG4 or ATR gene or carry a polymorphism in the BRCA2, XRCC4, LIG4 or ATR gene.

The method may be used to aid selection of an appropriate dose of USP4 inhibitor, in order to optimise treatment for each subject. The method may be used to determine the effectiveness of treatment with a USP4 inhibitor. For example, the method may be used to quantify the amount or proportion of cells in a sample of the cancer cells that include a defective BRCA2, Ligase IV, XRCC4 or ATR. A decrease or increase in this amount/proportion may indicate that the treatment with USP4 is effective.

In another embodiment the responsiveness of a subject to a USP4 inhibitor is determined by the presence of cancer cells resistant to platinum-based chemotherapy. Resistance is detected by the persistence or recurrence of tumour growth and/or the presence of metastasis following previous treatment with platinum-based chemotherapy. Alternatively the responsiveness of a subject is determined by an in vitro assay measuring survival of the tumour cells when exposed to platinum-based chemotherapy agents. Such methods are known to the skilled person in the art and the determination of whether a patient has a cancer resistant to platinum-based treatment is a routine assessment carried out by clinicians. Patients having cancer cells that respond to platinum-based chemotherapy for less than six months may be defined as having a cancer resistant to platinum-based treatment.

According to a further aspect of the invention there is provided a pharmaceutical composition comprising a USP4 inhibitor for use in the in the treatment of cancer combined with any pharmaceutically acceptable carrier, adjuvant or vehicle wherein the cancer comprises cells deficient in one or more DNA damage response (DDR) pathways.

A pharmaceutical composition may be a composition comprising an active agent and additionally one or more pharmaceutically acceptable excipients.

Suitable pharmaceutically acceptable excipients are known to those skilled in the art and generally include an acceptable composition, material, carrier, diluent or vehicle suitable for administering a USP4 inhibitor of the invention to an animal.

The animal may be a mammal, preferably a human.

The pharmaceutical compositions may be administered in any effective manner suitable effective for targeting cancer cells, for example by oral, intravenous, intramuscular, intranasal or topical methods. The pharmaceutical composition may be administered directly at the site of the tumour, for example during a surgical procedure or by intravenous methods.

Dosages may be varied depending on the requirements of the patient, the severity of the condition being treated and the characteristics of the active ingredient being employed. Determination of the effective dose is within the remit of the skilled person, without undue burden. Suitable dosage forms for administration to mammals, including humans are typically in the range of up to 100 mg/kg body weight, or may be 0.1 mg/kg, 10 mg/kg, 20 mg/kg, 30 mg/kg for example.

According to a further aspect of the invention there is provided a method of treating a subject having a cancer comprising cells resistant to platinum based chemotherapy and/or deficient in one or more DNA damage response (DDR) pathways, the method comprising administering to the subject a therapeutically effective amount of a USP4 inhibitor.

USP4 inhibitors may be selected from small molecules, peptides, oligonucleotides, an RNA-based drug (included but not limited to short interfering RNA (siRNA), short hairpin RNA (shRNA) and/or microRNA (miRNA)) molecule and antibodies. The USP4 inhibitor may be a small molecule compound.

The USP4 inhibitor may be administered alone.

The USP4 inhibitor may be administered prior to, in combination with or subsequent to the administration of an additional anti-tumour therapeutic agent, for example chemotherapeutic agents, radiation, or inhibitors of other DNA damage response proteins.

Such anti-tumour therapeutic agents have been extensively described earlier in the application.

Embodiments described in one aspect of the invention may also be combined in other aspects of the invention.

The invention is described further in the following non-limiting examples.

EXAMPLES

Materials and Methods

Cell Lines and Cell Culture

Human osteosarcoma U2OS cells were cultured at 37° C. in a humidified atmosphere and 5% (v/v) $CO_2$ in Dulbecco's modified eagle's medium (DMEM; Sigma-Aldrich) supplemented with 10% (v/v) fetal *bovine* serum (FBS; Gibco), 100 U/ml penicillin, 100 µg/ml streptomycin and 292 µg/ml L-Glutamine (Gibco). U2OS cells stably over-expressing GFP, GFP-USP4 WT, CD or RFP-53BP1 (Galanty et al., Nature 462, 935-939, 2009) were cultured in the presence of 0.5 mg/ml Geneticin (Gibco). U2OS cells stably expressing direct-repeat (DR)-GFP were cultured in the presence of 1 µg/ml puromycin (Sigma-Aldrich) and established as previously described (Pierce et al., 1999). DDR deficient HeLa isogenic Silencix cell lines (shATR, shBRCA2, shLigase IV, shXRCC4 and shControl) (tebu-bio) were grown in DMEM medium supplemented with 10% (v/v) fetal *bovine* serum (FBS; Gibco), 100 U/ml penicillin, 100 µg/ml streptomycin and 125 µg/ml hygromycin B (Invitrogen).

Example 1: USP4 Biochemical Assay

Figure 15:
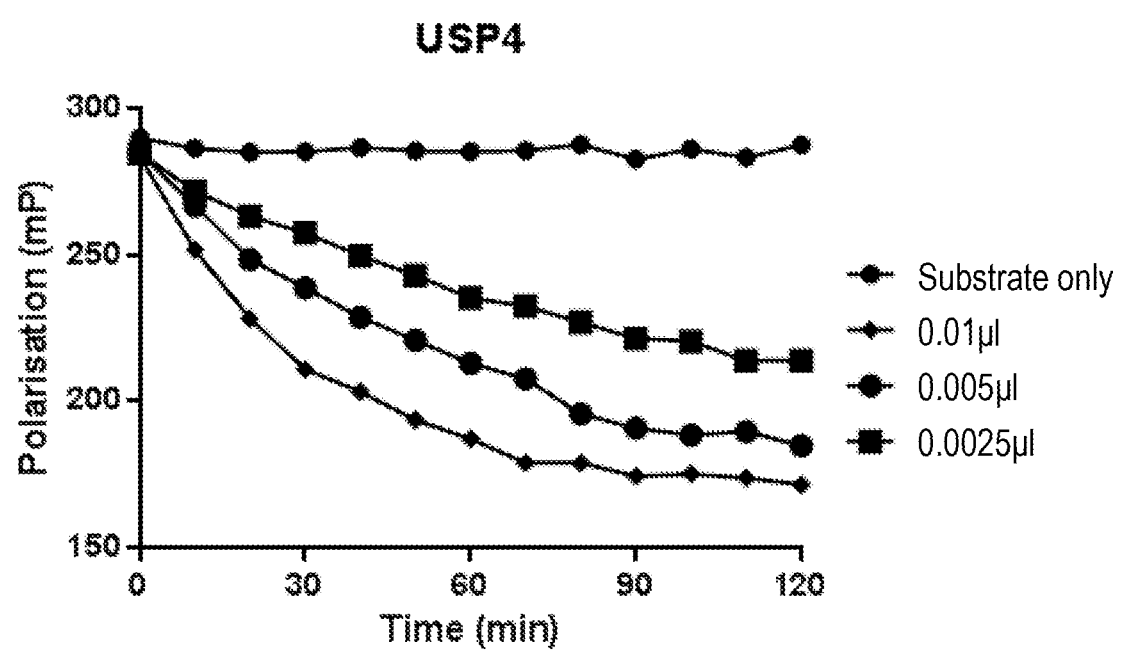
FIG. 15 is a graph showing the results of a USP4 biochemical assay, particularly, the proteolytic activity of purified FLAG-USP4 using a fluorescence polarisation assay. Various concentrations of USP4 as indicated were incubated with a TAMRA-labelled peptide linked to ubiquitin via an isopeptide bond and signal detected using florescence polarisation.

Reactions were performed in duplicate 5 in black 384 well plates (small volume, Greiner 784076) in a final reaction volume of 20 µl. USP4 was diluted in reaction buffer (20 mM Tris, pH 7.5, 100 mM NaCl, 0.05% Tween 20, 0.5 mg/ml BSA, 5 mM—beta mercaptoethanol) to the equivalent of 0, 0.01, 0.005, 0.0025 µl/well. Reactions were initiated by the addition of 100 nM of TAMRA labelled peptide linked to ubiquitin via an iso-peptide bond as fluorescence polarization substrate. Reactions were incubated at room temperature and read every 2 min for 120 min. Readings were performed on a PHERAstar Plus (BMG Labtech). λ Excitation 540 nm; λ Emission 590 nm. The results are shown in FIG. 15.

Example 2: Measuring Synthetic Lethality by Colony Forming Assay (CFA)

1.5 µl of 20 µM control or USP4-specific siRNAs were diluted in 0.5 ml OptiMEM serum-free medium containing 3.5 µl Lipofectamine RNAiMAX (Life Technologies), then incubated at room temperature for 10-20 min in the well of a 6 well plate. $2 \times 10^5$ cells in 2.5 ml medium was added to the transfection mixture then incubated overnight at 37° C., 5% $CO_2$. Control and matched DDR-deficient cells were then trypsinised, counted and diluted to 2000 cells per ml and 0.5 ml added to the wells of a 6 well tissue culture plate contain 1.5 ml of medium. The plates were returned to the incubator for 1-2 weeks until the colonies have formed to ≥50 cells per colony. The medium was then removed from the wells and replaced with 1 ml Giemsa stain for 10-20 min at room temperature. The stain was removed and the plates washed 4 times in tap water. The plates were dried overnight, scanned and the colonies counted using ImageJ software. The data was expressed as fraction of colonies in the control wells. The results are shown in FIG. 1

Example 3: Measuring Chemosensitisation and Fadiosensitisation by Colony Forming Assay (CFA)

Example 3a

Figure 6:
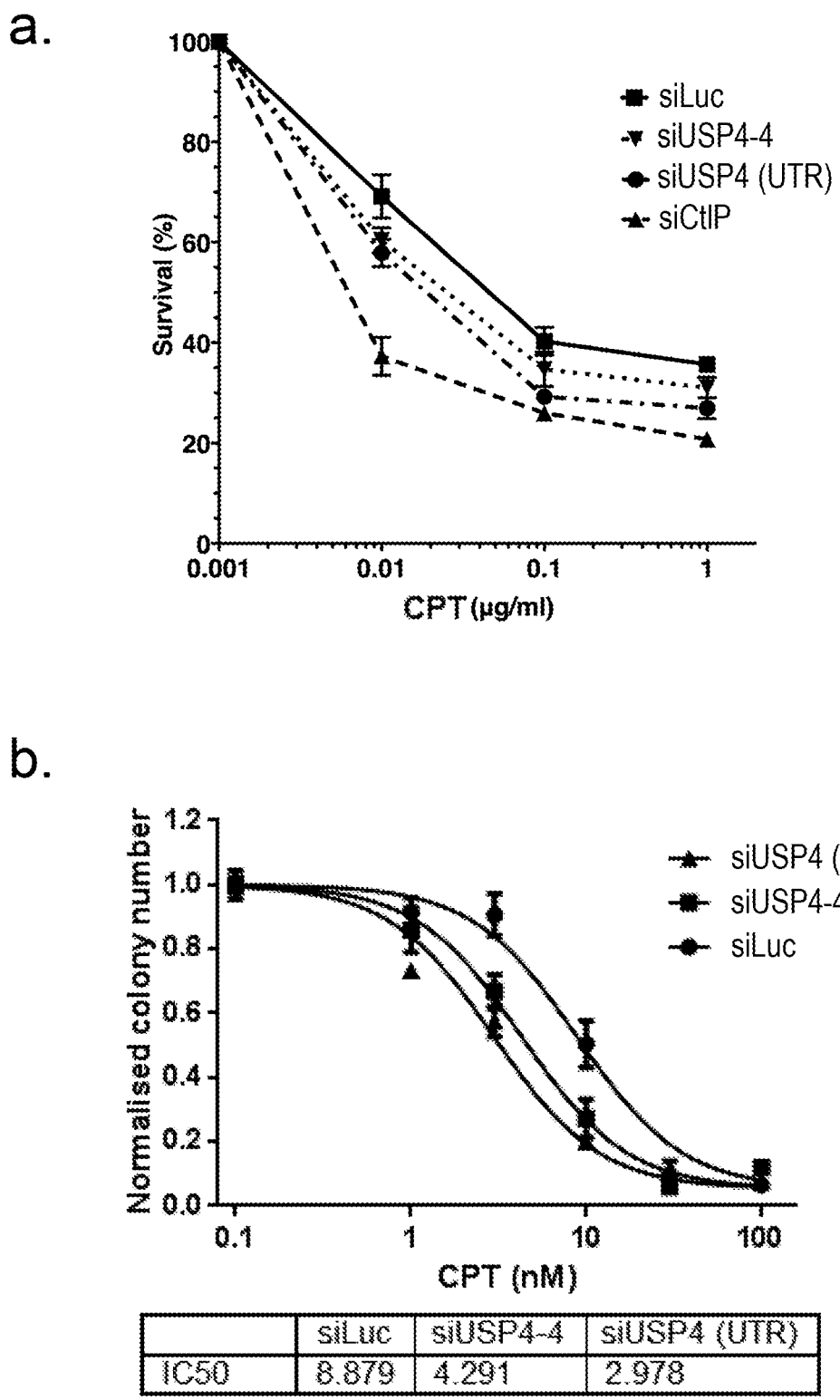
FIG. 6a is a graph showing siRNA knockdown of USP4 sensitises cancer cells to the Topoisomerase I inhibitor Camptothecin (CPT). Clonogenic survival of control (Luc or CtIP) or USP4 depleted (4-4 or 4 UTR) U2OS cells upon acute CPT exposure is shown (mean±s.e.m., n=3). Error bars represent SEM.
FIG. 6b is a graph showing siRNA knockdown of USP4 sensitises cancer cells to the Topo-isomerase I inhibitor Camptothecin (CPT). U2OS osteosarcoma cells were transfected with control (siLuc) or USP4-specific siRNAs targeting different USP4 regions (siUSP4 (UTR) or siUSP4-4) for 24 h before re-seeding into multi-well plates. Following an overnight incubation, the cells were treated with CPT. The cells were incubated for 9 days, and then the colonies were fixed in Giemsa stain and counted. Error bars represent SEM.
Figure 7:
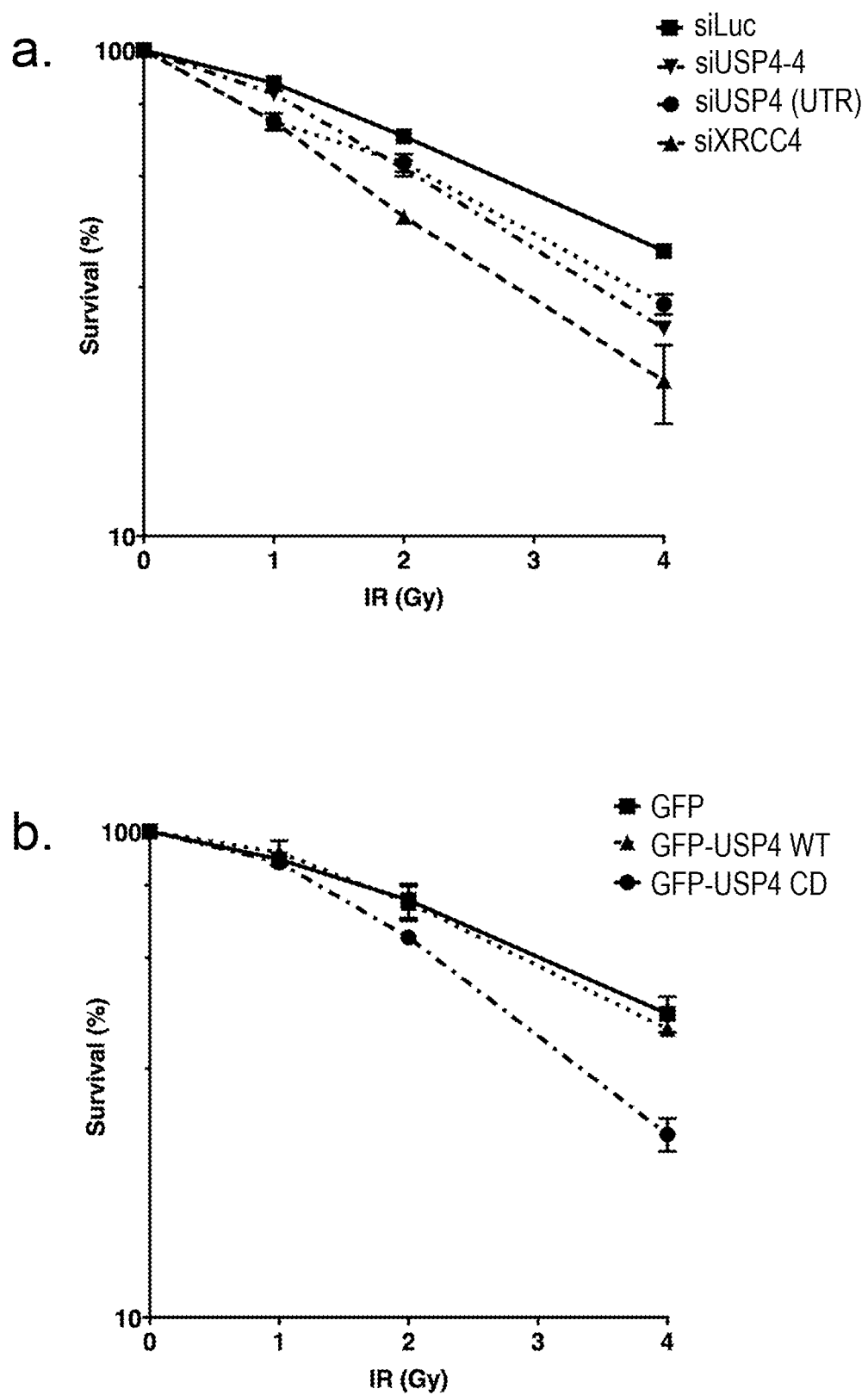
FIG. 7a is a graph showing USP4 sensitises cells to ionising radiation (IR). Clonogenic survival of USP4 depleted (4-4 or 4 UTR) U2OS cells upon acute IR treatment. The siRNAs targeting Luc or XRCC4 were negative or positive controls, respectively (mean±s.e.m., n=3).
FIG. 7b is a graph showing that over-expression of a catalytically-inactive USP4 sensitises cells to ionising radiation (IR). Clonogenic survival of U2OS cells stably expressing GFP or GFP-USP4 (WT—wild type or CD—catalytically dead) upon acute IR treatment (mean±s.e.m., n=3).
Figure 8:
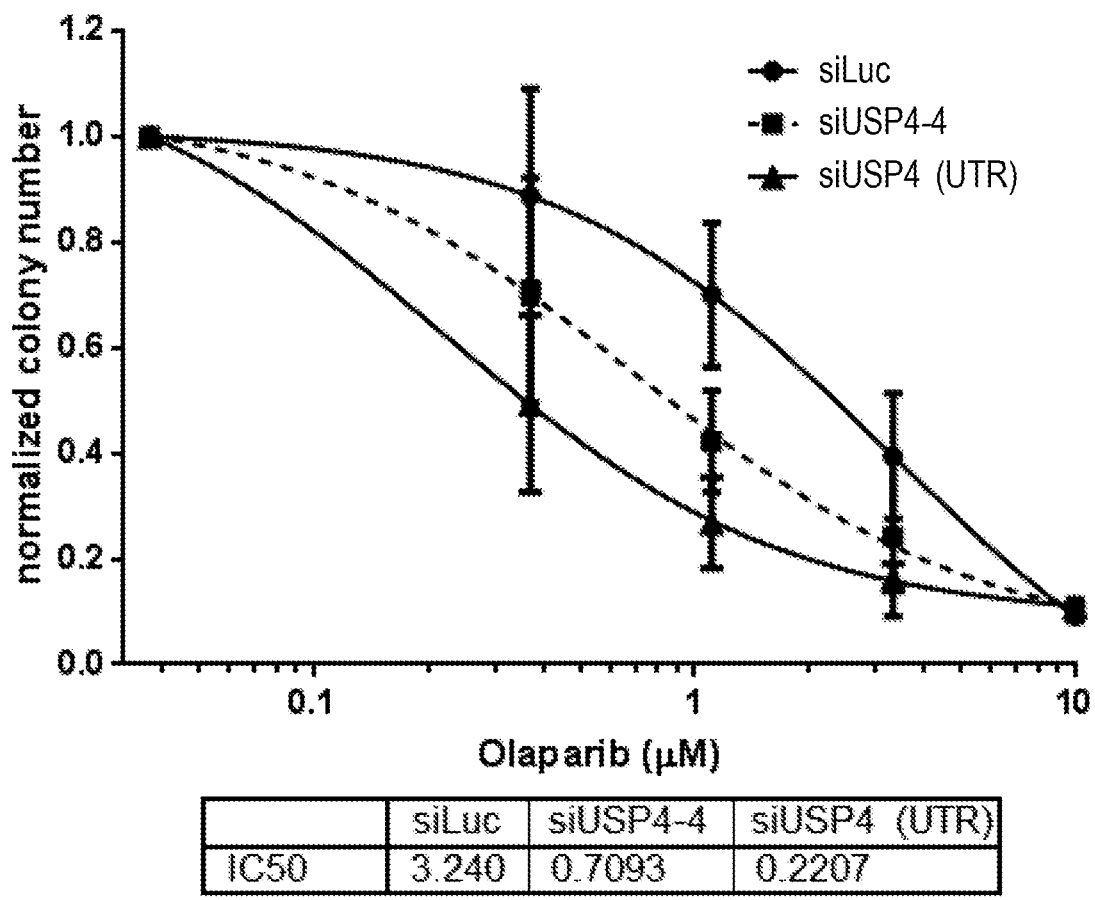
FIG. 8 is a graph showing siRNA knockdown of USP4 sensitises U2OS osteosarcoma cells to the PARP inhibitor olaparib. Cells were transfected with control (siLuc) or USP4-specific siRNAs targeting different USP4 regions (siUSP4-4 or siUSP4 (UTR)) for 24 h before re-seeding into multi-well plates. Following an overnight incubation, the cells were treated with olaparib. The cells were incubated for 9 days, and then the colonies were fixed in Giemsa stain and counted. Error bars represent SEM.

As Example 2, except that on the third day the cells (which had 24 hours earlier been seeded on 6 well plates, NUNC, at 250, 500 or 1,000 cells per well) were treated with serial dilutions of various chemotherapeutic agents by adding 20 µl of ×100 drug solution to the appropriate wells, or various acute doses of ionizing radiation [IR; (Faxitron X-Ray Corporation, Illinois, USA)]. The plates were then returned to the incubator and left for 1-2 weeks, and washed once with PBS and fixed and stained with crystal violet solution [2% (w/v) crystal violet (Sigma-Aldrich) in 10% (v/v) ethanol]. The results are shown in FIGS. 6a, 7a and 7b

Example 3b

Measuring Chemosensitisation by Colony Forming Assay (CFA)

As Example 2, except that on the third day the cells were treated with serial dilutions of various chemotherapeutic agents by adding 20 µl of ×100 drug solution to the appropriate wells. The plates were then returned to the incubator and left for 1-2 weeks, and Giemsa stained as mentioned above. The results are shown in FIGS. 3, 4, 5, 6b, 8.

Figure 2:
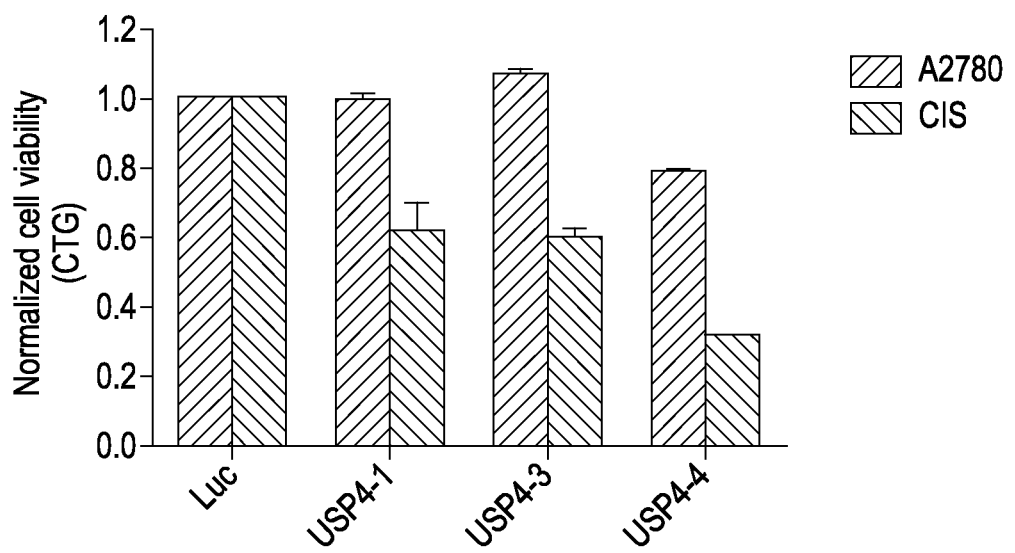
FIG. 2 is a graph showing knockdown of USP4 with specific siRNAs kills in vitro-derived platinum resistant cancer cells (CIS) preferentially as compared to platinum-sensitive cancer cells (A2780), via Cell Titer Glo assay. Cells were transfected with control (siLuc) or USP4-specific siRNAs targeting different USP4 regions (USP4-1, USP4-3 and USP4-4) for 16 h before re-seeding into multi-well plates. The cells were incubated for a further 96 h before addition of Cell Titer Glo. Cell viability was determined by measuring luminescence on the Clariostar plate reader. This data shows that USP4 knockdown preferentially kills platinum resistant cancer cells.
Figure 3:
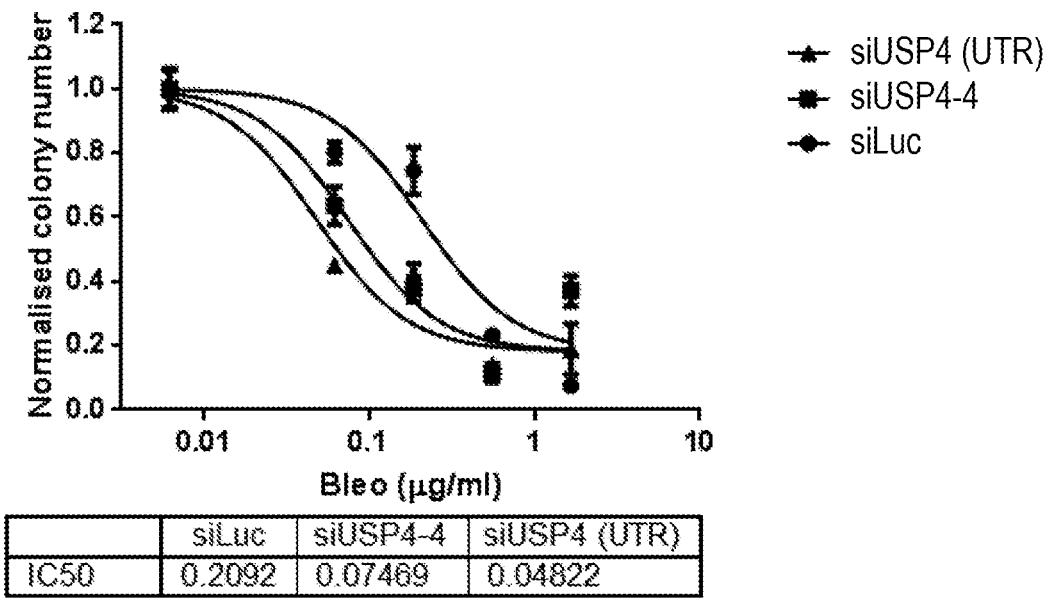
FIG. 3 is a graph showing siRNA knockdown of USP4 sensitises U2OS osteosarcoma cells to the radiomimetic Bleomycin. Cells were transfected with control (siLuc) or USP4-specific siRNAs targeting different USP4 regions (siUSP4-4 or siUSP4 (UTR)) for 24 h before re-seeding into multi-well plates. Following an overnight incubation, the cells were treated with Bleomycin. The cells were incubated for 9 days, and then the colonies were fixed in Giemsa stain and counted. Error bars represent SEM.
Figure 4:
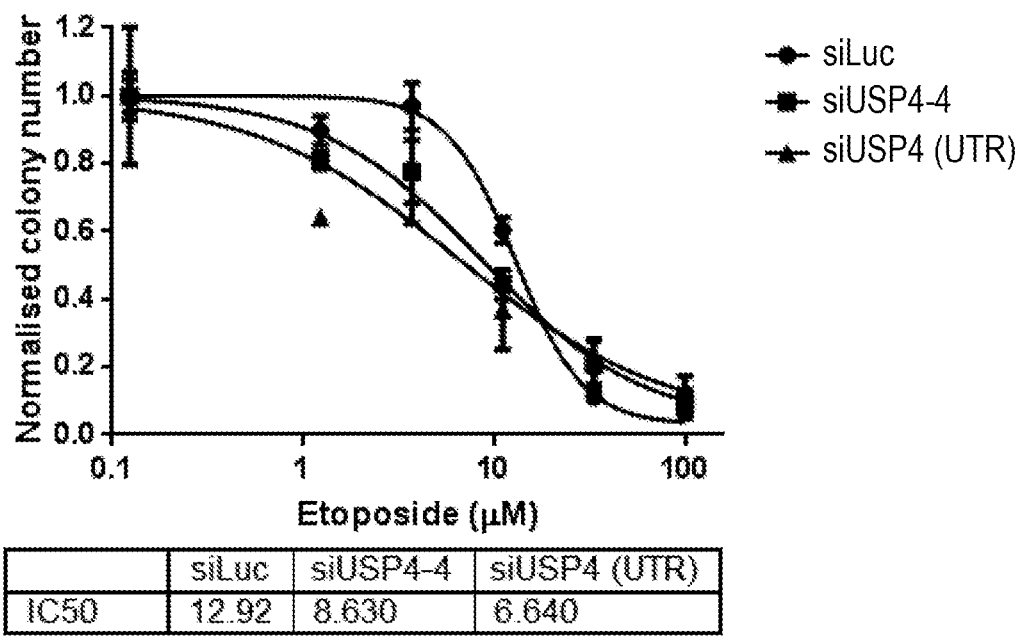
FIG. 4 is a graph showing siRNA knockdown of USP4 sensitises U2OS osteosarcoma cells to the Topoisomerase II chemotherapeutic agent (inhibitor) Etoposide. Cells were transfected with control (siLuc) or USP4-specific siRNAs targeting different USP4 regions (siUSP4-4 or siUSP4 (UTR)) for 24 h before re-seeding into multi-well plates. Following an overnight incubation, the cells were treated with Etoposide. The cells were incubated for 9 days, and then the colonies were fixed in Giemsa stain and counted. Error bars represent SEM.
Figure 5:
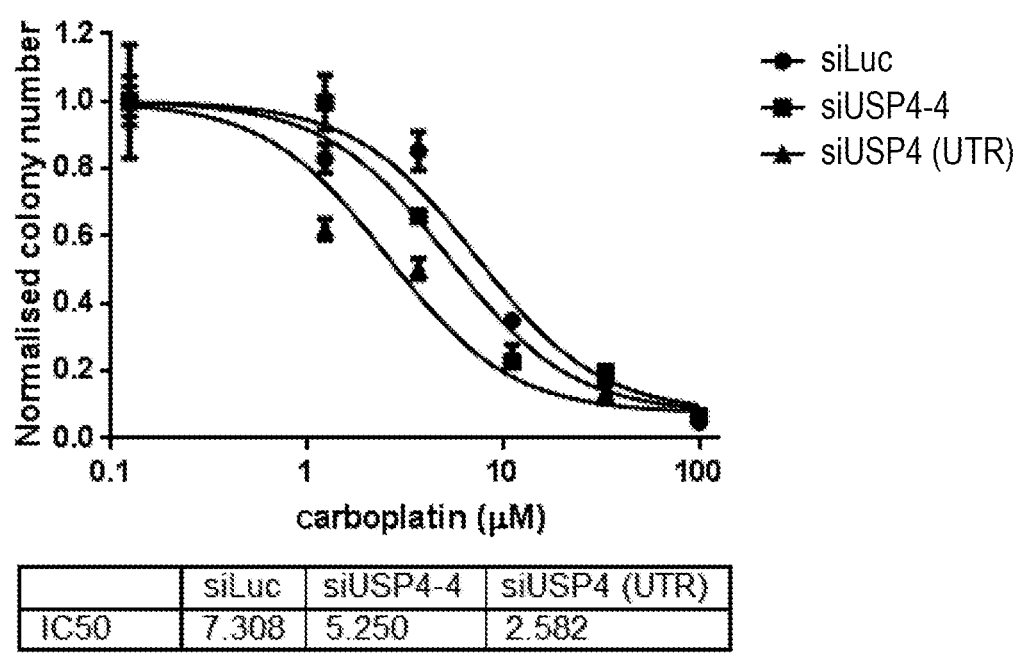
FIG. 5 is a graph showing siRNA knockdown of USP4 sensitises U2OS osteosarcoma cells to the platinating agent Carboplatin. Cells were transfected with control (siLuc) or USP4-specific siRNAs targeting different USP4 regions (siUSP4-4 or siUSP4 (UTR)) for 24 h before re-seeding into multi-well plates. Following an overnight incubation, the cells were treated with Carboplatin. The cells were incubated for 9 days, and then the colonies were fixed in Giemsa stain and counted. Error bars represent SEM.

Example 4: Measuring Selective Killing of Platinum-Resistant Tumour Cells Using CellTiter Glo 6 µl of 1 µM control or USP4-specific siRNAs were diluted in 80 µl OptiMEM serum-free medium containing 0.48 µl Lipofectamine RNAiMAX. Transfection mixtures were then incubated at room temperature for 90 min. 20 µl of each transfection complex was spotted into 4 wells of a 96 well plate. Cells were then trypsinised, counted and diluted to 34800 cells/ml (A2780), 52200 cells/ml (A2780CIS), in RPMI+10% FBS+2 mM Sodium Pyruvate. 115 µl of each cell suspension was added to 1 wells of each transfection complex. Cells were incubated under normal growth conditions (37° C. and 5% $CO_2$) for a further 4 days. Then, 50 µl of reconstituted CellTiter Glo reagent (Promega) was added to each well. The plates were placed on a plate shaker for 4 minutes and luminescence was read after 10 more minutes using the Clariostar plate reader. The results are shown in FIG. 2.

Example 5: Expression Vectors

The pEGFP-GW-JJ-USP4 (accession number: NM_003363) expressing enhanced green fluorescent protein (GFP)-USP4 wild-type (WT) was a provided by Michael J.

Clague and Sylvie Urbé (Institute of Translational Medicine, University of Liverpool). The catalytic dead (CD) GFP-USP4 mutant (C311A) was generated from the pEGFP-GW-JJ-USP4 plasmid using the QuikChange Lightning site-directed mutagenesis kit (Agilent Technologies). Results using these vectors are shown in FIGS. 7 and 9 to 11.

Example 6: siRNA Transfection

U2OS cells ($4.8\times10^5$ cells/6 cm dish) were transfected with 30 nM siRNA using HiPerFect (Qiagen) transfection reagent according to the manufacturer's protocol, followed 24 hours later by a second identical transfection. The USP4 pool of 4 siRNAs was obtained from Qiagen and all other siRNAs from Eurofins MWG Operon. Sample treatment and analysis were performed 72 hours after initial transfection. The siRNA sequences used in this application are described in table 1. siRNA knockdown was performed in order to obtain the data in several experiments and was used in order to obtain the data for FIGS. 1 to 9 and 11 to 13.

protein concentrations were determined with the Bradford protein assay (Thermo Scientific). Ten microgram of soluble fraction or the corresponding amount of chromatin fraction was boiled for 5 minutes at 95° C. in loading-buffer [67 mM Tris-HCl (pH 6.8), 2% (w/v) sodium dodecyl sulfate (SDS) (MP Biomedicals). 10% (v/v) Glycerol (Sigma) and 0.002% (w/v) Bromophenol Blue (Sigma) in milliQ water)], loaded on a 4-12% Bis/Tris acrylamide gel (Invitrogen) and separated at 120 V for 2 hours with NuPAGE® MOPS SDS Running Buffer (Invitrogen). The proteins were transferred onto nitro-cellulose membranes (Millipore), after which the membranes were blocked in Tris-buffered saline containing 0.1% (v/v) Tween-20 (TBS-T; Sigma-Aldrich) and 1% (w/v) *bovine* serum albumin (BSA; Sigma-Aldrich) and incubated with appropriate primary and secondary antibodies summarized in supplemental table 2. Routine chemiluminescent protein detection was carried out upon horseradish peroxidase (HRP) conjugated secondary antibody treatment, with the ECL western blotting system according to the manufac-

TABLE 1

Synthetic small interfering RNAs

| SEQ ID No. | Name | Abbr. | Sequence | Supplier | Target | CDS/3-UTR |
|---|---|---|---|---|---|---|
| 3 | Luciferase (Luc) | Luc | AACGUACGCGGAAUACUUCGA | MWG Operon | non-targeting | CDS |
| 4 | siUSP4-1 | 4-1 | ACCGAGGCGUGGAAUAAACUA | Qiagen | USP4 | CDS |
| 5 | SiUSP4-2 | 4-2 | UAGAUGAAUUAAGACGGUUAA | MWG Operon | USP4 | CDS |
| 6 | siUSP4-3 | 4-3 | CAGGCAGACCUUGCAGUCAAA | MWG Operon Or Qiagen | USP4 | CDS |
| 7 | siUSP4-4 | 4-4 | CACCUACGAGCAGUUGAGCAA | MWG Operon Or Qiagen | USP4 | CDS |
| 8 | siUSP4 3'-UTR | 4 UTR | UUAAACAGGUGGUGAGAAA | MWG Operon | USP4 | UTR |
| 9 | siCtIP | CtIP | GCUAAAACAGGAACGAAUC | MWG Operon | CtIP | CDS |
| 10 | siCRXCR | CRXC4 | AUAUGUUGGUGAACUGAGA | MWG Operon | XRCC4 | CDS |
| 11 | siLigaseIV | LigIV | AGGAAGUAUUCUCAGGAAUUA | MWG Operon | LigaseIV | CDS |
| 12 | siBRCA1 | BRCA1 | GGAACCUGUCUCCACAAG | MWG Operon | | |

Example 7: Cell Extract Preparation and Immunoblotting

Cells were lysed on ice for 30 minutes with 300 µl/6 cm dish CSK-buffer [300 mM sucrose, 3 mM $MgCl_2$, 10 mM piperazine-N,N'-bis(2-ethanesulfonic acid) (PIPES; pH 6.8), 1 mM ethylene glycol tetra-acetic acid (EGTA), 0.1% Triton X-100 (Sigma), protease inhibitor cocktail (Roche), phosphatase inhibitor cocktail (Sigma-Aldrich) and 10 mM N-Ethylmaleimide (NEM; Sigma-Aldrich)] containing 300 mM NaCl. Soluble and chromatin fractions were separated by centrifugation (20,000×g for 10 minutes at 4° C.). Chromatin fractions were sonicated on ice (30% amplitude; Sonics Vibra Cell, VHX 500 Watt) for 15 seconds and turer's protocol (Amersham). Quantitative western blot analysis was carried out upon Alexa-fluor conjugated secondary antibody treatment. Membranes were scanned with an Odyssey Li-Cor imaging system and protein quantification was achieved using Odyssey v1.2 software (LI-COR Biosciences UK Ltd). Data from these experiments is shown in FIGS. 9a, 9c and 9e.

Example 8: Neutral Single Cell Electrophoresis

Figure 9:
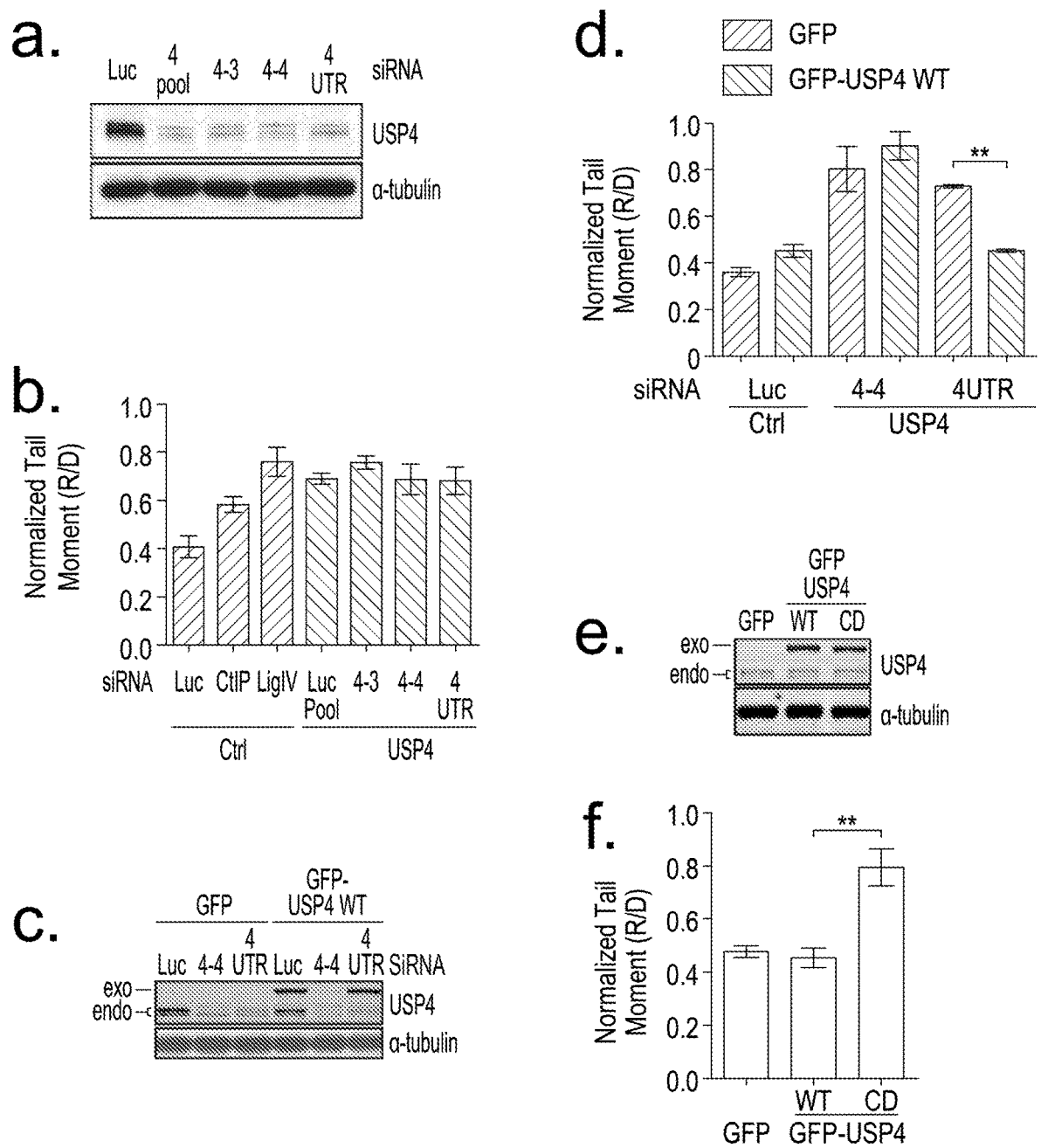
FIG. 9a shows an image of a protein immunoblot demonstrating the knockdown efficiency of USP4 in U2OS cells by a pool of four siRNAs (4 Pool: siUSP4-1, 4-2, 4-3 and 4-4). Two individual siRNAs targeting the coding sequence (4-3 or 4-4) or the 3' untranslated region targeting siRNA (4 UTR) was assessed by immunoblotting analysis with indicated antibodies. The siRNA targeting Luciferase (Luc) is a negative control. α-tubulin was used as loading control.
FIG. 9b is a graph showing neutral single cell electrophoreses (NSCE)-assay of USP4 depleted (4 pool, 4-3, 4-4, or 4 UTR) U2OS cells upon phleomycin treatment. siRNAs targeting Luc, CtIP or Ligase IV (Lig IV) are controls, the latter two are positive controls (CtIP and Lig IV are proteins involved in double strand break repair), (mean±s.e.m., n=3).
FIG. 9c shows an image of a protein immunoblot. GFP or GFP-USP4 WT expressing U2OS cells were transfected with indicated siRNAs and subjected to immunoblotting analysis with indicated antibodies. Bars and brackets indicate exogenous (exo.) or endogenous (endo.) USP4 respectively. α-tubulin was used as a loading control.
FIG. 9d is a graph showing NSCE complementation assay carried out as in FIG. 9b with GFP or GFP-USP4 expressing cell lines transfected with the indicated siRNAs (mean±s.e.m., n=2).
FIG. 9e shows an image of a protein immunoblot. Stable cell line establishment: U2OS cells expressing GFP or GFP-USP4 (WT or CD). Cell extracts were analysed by immunoblotting with the indicated antibodies. α-tubulin was used as loading control.
FIG. 9f is a graph showing NSCE assay performed with cell lines described in FIG. 9e (mean±s.e.m., n=3). (** P <0.01).
Figure 10:
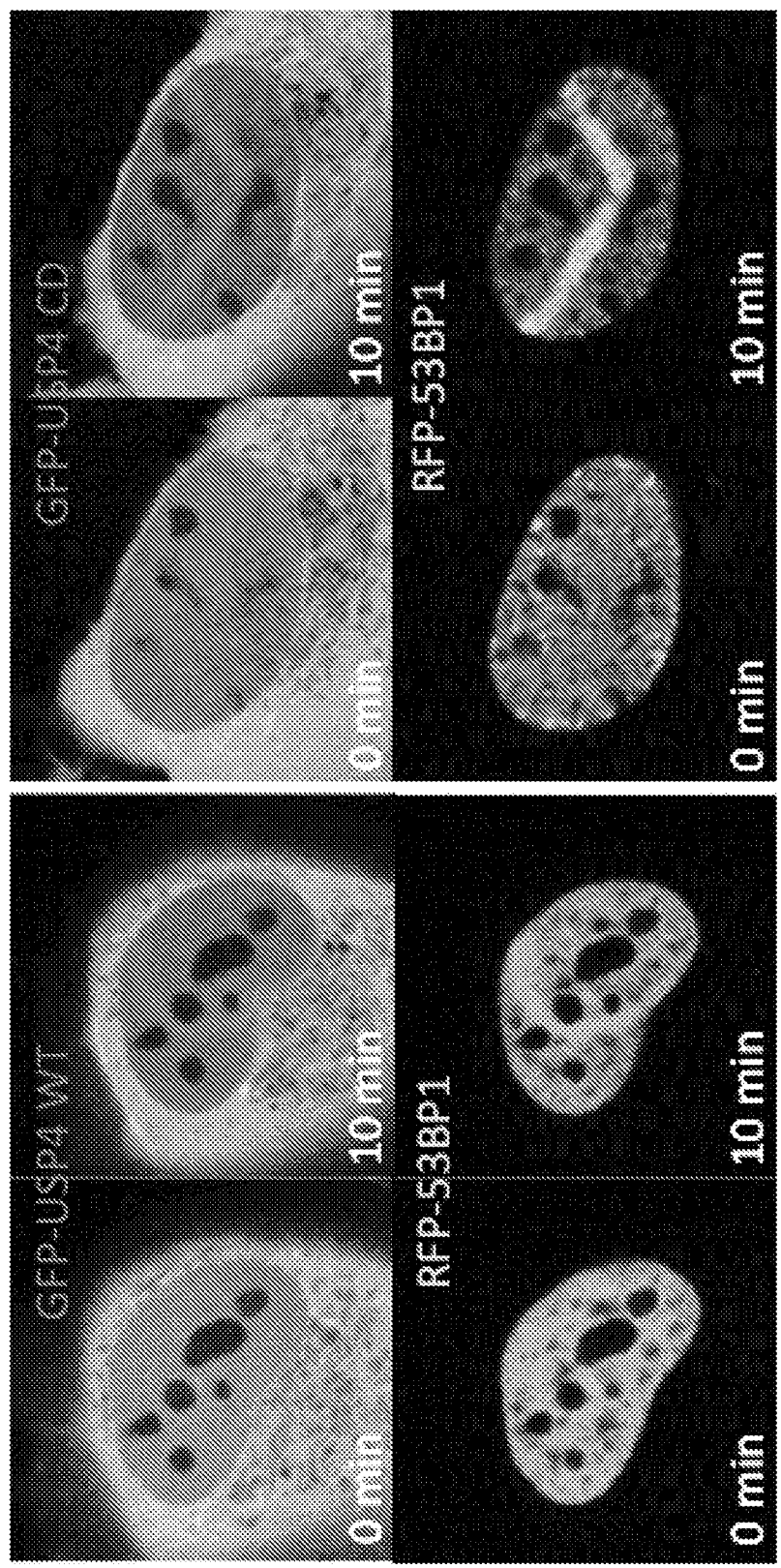
FIG. 10 shows images of U2OS cells stably expressing RFP-53BP1 transiently transfected with GFP-USP4 WT or CD plasmids and subjected to laser micro-irradiation. Pictures were taken before and 10 minutes after irradiation. RFP-53BP1 was used to visualize the site of DNA damage. USP4 is recruited to sites of laser micro-radiation independent of its catalytic activity.
Figure 11:
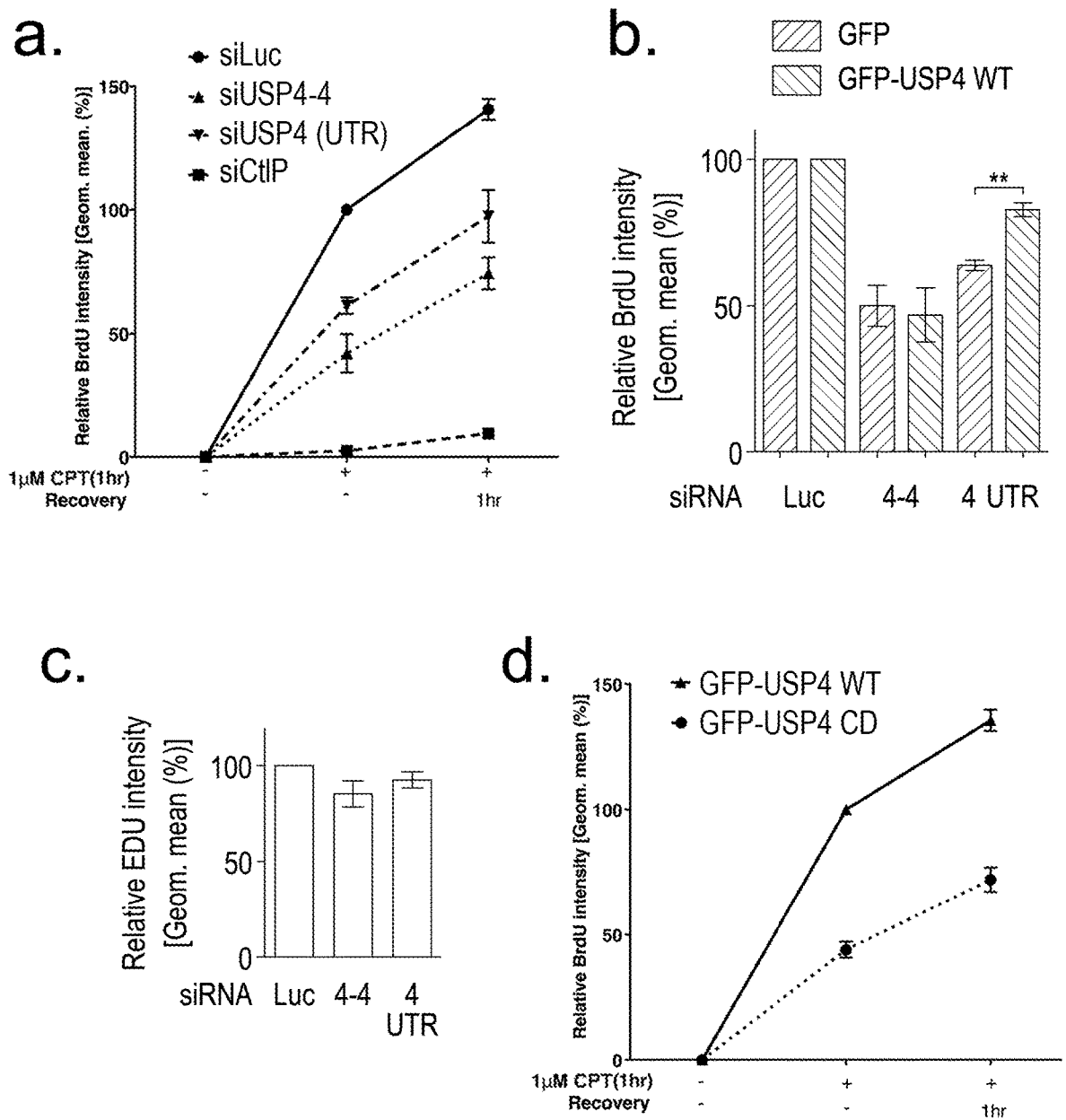
FIG. 11a is a graph showing quantitative ssDNA formation assay. Single-strand DNA formation following treatment with CPT (1 μm) was assessed in U2OS cells transfected with control (Luc or CtIP) or USP4 (4-4 or 4 UTR) siRNAs. BrdU signal intensity was normalized to the control (siLuc) (mean±s.e.m., n=3).
FIG. 11b is a graph showing quantitative ssDNA formation assay in U2OS cells stably expressing GFP or GFP-USP4 WT transfected with control (Luc) or USP4 targeting (4-4 or 4 UTR) siRNAs. Relative signal BrdU intensity was assessed by normalization to their respective CPT and control (siLUC) GFP cells which were set to 100% (mean±s.e.m., n=3). (**P<0.01).
FIG. 11c is a graph showing Control (Luc) or USP4 depleted (4-4 or 4 UTR) U2OS cells pulse labelled with EdU. The relative EdU signal intensity was calculated and normalised to Luc, which was set to a 100% (mean±s.e.m., n=2). This demonstrates that the effect seen in FIG. 11b is not due to a general cell-cycle effect.
FIG. 11d is a graph showing quantitative DNA-end resection assay in GFP-USP4 WT or CD expressing U2OS cells (mean±s.e.m., n=5).

Cells were treated with phleomycin (40 µg/ml; Sigma-Aldrich) for 2 hours. Subsequently, cells were washed twice with phosphate buffered saline (PBS) and left to recover for 2 hours under normal cell culture conditions. Cells were then washed once with PBS (−/−) (Gibco) and scraped off, after which the pellets were resuspended in PBS (−/−) at an approximate concentration of 5×10⁶ cells/ml. 10 µl of cell suspension was then mixed with 90 µl LMAgarose (37° C.; Trevigen) after which 70 µl was spotted onto GelBond Film (Lonza), covered by a 22 mm cover glass (VWR) and incubated at 4° C. for 10 minutes. Upon cover glass removal, the samples were incubated in lysis solution (Trevigen) for 1 hour at 4° C. Lysis solution was washed off with TBE [90 mM Tris-Borate, pH 8.3 and 2 mM 2,2',2",2'''-(Ethane-1,2-diyldinitrilo)tetra-acetic acid (EDTA)] and subjected to electrophoresis under 35 V current for 7 minutes in TBE. After fixation in 70% (v/v) ethanol for 5 minutes, the samples were dried overnight and stained with SYBR green nucleic acid staining solution (Invitrogen). Pictures were taken with an Olympus IX71 microscope, connected to a Lumen2000 Prior stage, an FView soft imaging camera and Cell^F analysis imaging software. Per condition, tail-moments of 50 individual cells were quantified with CometScore software (Tritek Corp.). Results are shown in FIGS. 9$b$, 9$d$ and 9$f$.

Example 9: Live Cell Laser-Line Micro-Irradiation

Twenty-four hours after seeding, U2OS cells stably expressing RFP-53BP1 [12×10⁴ cells/35 mm glass bottom dish (Ted Pella, Inc)] were transfected with 1 µg pEGFP-GW-JJ-USP4 WT or CD with TransIT-LT1 transfection reagent (Mirus Biologicals) according to the manufacturer's protocol. Twenty-four hours after transfection the cells were pre-sensitized with 10 µM 5-bromo-2'-deoxyuridine (BrdU) for 24 hours and subsequently subjected to 400 µW localized laser micro-irradiation with a 405 nm UV-A laser beam (Limoli and Ward, 1993). Photographs of the cells are shown as FIG. 10.

Example 10: Immunofluorescence Staining

Control (Luc or BRCA1) or USP4 (4 UTR) depleted cells were exposed to 5 gy IR and left to recover for 8 hours. U2OS cells, cultured on poly-L-lysine [0.01% (w/v); Sigma-Aldrich] coated coverslips, were washed twice with PBS and fixed with 2% (w/v) paraformaldehyde (PFA; Sigma-Aldrich) at room temperature for 20 minutes. Cells were then washed twice with PBS containing 0.1% Tween-20 (PBS-T; Sigma-Aldrich) and permeabilized with 0.1% (v/v) Triton X-100 (in PBS) for 5 minutes at room temperature. Following incubation in block-buffer [5% (v/v) FBS in PBS] for 30 minutes at room temperature the cells were incubated with anti-RAD51 and anti-γH2AX primary antibodies at room temperature for 2 hours and their respective secondary antibodies at room temperature for 1 hour, summarized in table 2. The cells were finally stained with 1 µg/ml 4',6-diamidino-2-phenylindole (DAPI) for 10 minutes at room temperature, mounted onto microscope slides (VWR) using VECTASHIELD mounting medium (Vector Laboratories), and analyzed with a confocal microscope (1×81 Olympus) with software for image acquisition. The results are shown in FIG. 12$a$.

TABLE 2

| | | | Antibodies | | | | |
|---|---|---|---|---|---|---|---|
| | | | | | Applications and Dilutions | | |
| No. | Name | Species | Supplier | Cat no. | IB | IF | End-Res |
| 1 | USP4 | Rabbit | Bethyl | A300-830A | 1000x | | |
| 2 | BrdU | Mouse | Amersham Biosciences | RPN20AB | | | 200x |
| 3 | RAD51 | Rabbit | Santa Cruz | sc-8349 | | 200x | |
| 4 | GFP | Mouse | Roche | 11 814 460 001 | 1000x | | |
| 5 | IRDye 680CW Donkey IgG (H + L) | Mouse | Licor | 926-32213 | 10000x | | |
| 6 | IRDye 800CW Donkey IgG (H + L) | Rabbit | Licor | 926-68024 | 10000x | | |
| 7 | Goat anti Rabbit IgG-HRP | Rabbit | Pierce | 1858415 | 1000x | | |
| 8 | Goat anti Mouse IgG-HRP | Mouse | Pierce | 1858413 | 1000x | | |
| 9 | Alexa Fluor ® 488 Goat Anti-Mouse IgG (H + L) | Mouse | Molecular Probes | A11029 | | 1000x | 1000x |
| 10 | Alexa Fluor ® 488 Goat Anti-Rabbit IgG (H + L) | Rabbit | Molecular Probes | A11034 | | 1000x | 1000x |
| 11 | Alexa Fluor ® 594 Goat Anti-Mouse IgG (H + L) | Mouse | Molecular Probes | A11032 | | 1000x | 1000x |
| 12 | Alexa Fluor ® 594 Goat Anti-Rabbit IgG (H + L) | Rabbit | Molecular Probes | A11037 | | 1000x | 1000x |
| 13 | Alexa Fluor ® 647 Goat Anti-Rabbit IgG (H + L) | Rabbit | Molecular Probes | A21245 | | 1000x | 1000x |

IB: immunoblotting
IF: Immunoflourescence
End-Res.: End-Resection assay

Example 11: Quantitative DNA-End Resection Assay

U2OS cells were exposed to 30 µM BrdU for 24 hours, 48 hours after the initial siRNA transfection, and then treated with 1 µM camptothecin for 1 hour. When indicated, camptothecin was removed by washing the cells twice with PBS. Cells were then left to recover for 1 hour. After treatment, cells were washed twice with PBS, scraped off and resuspended in 500 µl PBS. The cell suspensions were fixed with ice-cold 70% (v/v) ethanol and stored overnight at −20° C. The fixed cells were washed twice with PBS-T, incubated in block-buffer (5% FBS in PBS; 30 minutes, room temperature) and incubated with anti-BrdU and anti-γH2AX primary antibodies and different combinations of secondary antibodies in block-buffer, summarized in supplementary table 2. After antibody treatment BrdU and γH2AX intensity was measured with the BD LSRFortessa cell analyzer (BD Biosciences) in the presence of 1 µg/ml DAPI. The BrdU intensity of S-phase gated cells was quantified with FlowJo software (Tree Star Inc) and the untreated samples were subtracted from the treated samples to normalize for the BrdU staining background. γH2AX intensities were used as a control for DNA damage. The results are shown in FIGS. 11a, 11b and 11d.

Example 12: Flow Cytometric DNA Replication Analysis

Seventy-two hours after the initial siRNA transfection, U2OS cells were exposed to 10 µM 5-ethynyl-2′-deoxyuridine (EdU) for 15 minutes, washed twice with PBS and fixed in 2% PFA (w/v) at room temperature for 20 minutes. Subsequently, cells were washed twice with PBS and permeablized with 0.2% Triton-X-100 (5 minutes at room temperature), washed once (PBS) and incubated in 100 µl/sample 'click-it' solution [20 µg/ml Click-iT® EdU buffer, 20 mM $CuSO_4$ and 1:500 diluted Alexa Fluor 647 azide in PBS (Molecular probes) for 30 minutes at room temperature, protected from the light. The EdU signal intensity was measured with the BD LSRFortessa cell analyzer and quantified with FlowJo software. Results are shown on FIG. 11c.

Example 13: DR-GFP HR Reporter Assay

The homologous recombination (HR) repair assay using U2OS cells, stably expressing the DR-GFP reporter, was carried out based on a previously established methodology (Pierce et al., 1999, Genes Dev., 13(20): 2633-8)). Briefly, DR-GFP cells were, 72 hours after siRNA-mediated depletion, transfected with 4 µg of different plasmid combinations as described below, using the TransIT-LT1 transfection reagent according to the manufacturer's protocol. To induce DSBs, the expression plasmid coding restriction enzyme I-SceI (3.75 µg; per sample pCBA I-SceI) was transfected together with the expression plasmid for red fluorescent protein (RFP; 0.25 µg; pCS2-mRFP) to monitor transfection efficiency. As a negative control, a combination of the empty plasmid [pCDNA3.1 (+)] and pCS2-mRFP was transfected (3.75 µg and 0.25 µg respectively). Forty-eight hours after plasmid transfection the cells were washed twice with PBS, detached using 0.1% EDTA in PBS, and collected in PBS with 5% (w/v) FBS. To be able to exclude dead cells, 1 µg/ml DAPI was added, and the HR efficiency was measured as the amount of GFP and RFP double positive cells normalized to the background-GFP control population, with the BD LSRFortessa cell analyzer. The results are shown in FIG. 12b.

Example 14: Random Plasmid Integration

The pEGFP-C1 plasmid (Clontech), containing a geneticin selection marker, was linearized by BamHI and XhoI restriction digestion according to the manufacturer's protocol (New England Biolabs). Seventy-two hours after the initial siRNA transfection, 5 µg/6 cm dish linearized plasmid was transfected into U2OS cells with the TransIT-LT1 transfection reagent according to the manufacturer's protocol. Six hours later the cells were seeded into 15 cm dishes at 4 different concentrations ($1.0 \times 10^3$, $2.5 \times 10^3$, $1.0 \times 10^4$ and $2.0 \times 10^4$ cells/dish). Twenty-four hours after re-seeding the plates containing $1.0 \times 10^4$ and $2.0 \times 10^4$ cells were cultured in presence and the plates containing $1.0 \times 10^3$ and $2.5 \times 10^3$ cells in absence of 1 mg/ml of geneticin for 10 to 14 days and stained with 2% (w/v) crystal violet solution. Plasmid integration efficiency was analyzed as the percentage of geneticin-resistant cells normalized to the transfection efficiency, calculated as the percentage of GFP positive cells by flow-cytometry with the FACS Calibur (BD Biosciences) 24 hours after plasmid transfection. Results are shown in FIG. 13. Luc or LigIV are the negative and positive control cells, respectively, and USP4(4-4 or 4UTR) are the USP4 depleted cells.

Example 15: Expression and Purification of USP4

The USP4 construct was PCR amplified and cloned into a pFLAG-CMV-6a vector (Sigma-Aldrich) with an N-terminal FLAG tag. HEK293T cells were transfected with FLAG-USP4 using TransIT-LT1 transfection reagent (Minis) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 1200 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound USP4, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3×FLAG peptide (Sigma-Aldrich)) was added to the resin and incubated at 4° C. for 2.5 hours rotating. The resin was centrifuged at 4000 rpm for 30 seconds, and the supernatant containing purified FLAG-USP4 was removed and stored at −80° C. Results are shown in FIG. 14, which is a gel photograph of purified FLAG-USP4.

The invention claimed is:

1. A method of treating cancer, comprising the step of administering a Ubiquitin Specific Protease 4 (USP4) inhibitor to a subject in need thereof, wherein the cancer comprises cells deficient in one or more DNA damage response (DDR) pathways and/or cells resistant to platinum-based chemotherapy, wherein the USP4 inhibitor is an RNA-based drug and the cancer is bone cancer or cervical cancer.

2. The method according to claim 1, wherein said one or more DDR pathways is selected from homologous recombinational repair, non-homologous end-joining repair and double-strand break repair.

3. The method according to claim 1, wherein deficiencies in one or more DDR pathways are due to mutations in, the absence of, or a defective expression of a gene encoding proteins selected from one or more of BRCA2, Ligase IV, XRCC4 and ATR.

4. The method according to claim 1, wherein the USP4 inhibitor causes a reduction in functional activity of USP4.

5. The method according to claim 1, wherein the RNA-based drug is a short interfering RNA (siRNA).

6. The method according to claim 5, wherein the USP4 inhibitor is selective for USP4.

7. The method according to claim 1, wherein said cancer is bone cancer.

8. The method according to claim 1, wherein the USP4 inhibitor is combined with an anti-tumour therapeutic agent.

9. The method according to claim 1, wherein said cancer is cervical cancer.

* * * * *